United States Patent
Romanak et al.

(10) Patent No.: US 9,816,972 B2
(45) Date of Patent: Nov. 14, 2017

(54) PROCESS-BASED APPROACH FOR THE DETECTION OF CO2 INJECTATE LEAKAGE

(71) Applicant: Board of Regents, The University of Texas System, Austin, TX (US)

(72) Inventors: Katherine Romanak, Austin, TX (US); Philip C. Bennett, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 86 days.

(21) Appl. No.: 14/317,836

(22) Filed: Jun. 27, 2014

(65) Prior Publication Data
US 2015/0000374 A1    Jan. 1, 2015

Related U.S. Application Data

(60) Provisional application No. 61/840,234, filed on Jun. 27, 2013.

(51) Int. Cl.
    *G01N 33/04*     (2006.01)
    *G01N 33/00*     (2006.01)
    (Continued)

(52) U.S. Cl.
CPC ........ *G01N 33/0004* (2013.01); *G01M 3/226* (2013.01); *G01N 33/004* (2013.01); *G01N 33/24* (2013.01); *G01V 9/00* (2013.01)

(58) Field of Classification Search
CPC .. G01N 33/0004; G01N 33/24; G01N 33/004; G01V 9/00; G01M 3/226
(Continued)

(56) References Cited

U.S. PATENT DOCUMENTS 7,704,746 B1 * 4/2010 White ............... E21B 41/0064
    436/56
8,681,336 B2 * 3/2014 Nickerson ............ G01N 21/85
    356/402
(Continued)

FOREIGN PATENT DOCUMENTS

WO    2014210509 A1    12/2014

OTHER PUBLICATIONS

Whalen, et al., Rapid methane oxidation in a landfill cover soil Applied Environmental Microbiology, 56(11): 3405-3411 (Nov. 1990).
(Continued)

*Primary Examiner* — Natalie Huls
*Assistant Examiner* — Monica S Young
(74) *Attorney, Agent, or Firm* — Kilpatrick Townsend & Stockton LLP

(57) ABSTRACT

The present invention includes a method for distinguishing between a natural source of deep gas and gas leaking from a $CO_2$ storage reservoir at a near surface formation comprising: obtaining one or more surface or near surface geological samples; measuring a $CO_2$, an $O_2$, a $CH_4$, and an $N_2$ level from the surface or near surface geological sample; determining the water vapor content at or above the surface or near surface geological samples; normalizing the gas mixture of the $CO_2$, the $O_2$, the $CH_4$, the $N_2$ and the water vapor content to 100% by volume or 1 atmospheric total pressure; determining: a ratio of $CO_2$ versus $N_2$; and a ratio of $CO_2$ to $N_2$, wherein if the ratio is greater than that produced by a natural source of deep gas $CO_2$ or deep gas methane oxidizing to $CO_2$, the ratio is indicative of gas leaking from a $CO_2$ storage reservoir.

21 Claims, 21 Drawing Sheets

(51) Int. Cl.
*G01V 9/00* (2006.01)
*G01N 33/24* (2006.01)
*G01M 3/22* (2006.01)

(58) Field of Classification Search
USPC .......................................................... 73/23.35
See application file for complete search history.

(56) References Cited

U.S. PATENT DOCUMENTS

| | | | | |
|---|---|---|---|---|
| 8,714,034 B2* | 5/2014 | Zimbron | ............ | B01D 53/0415 73/863 |
| 8,772,720 B2* | 7/2014 | Chae | ....................... | G01N 21/35 250/338.1 |
| 2010/0241363 A1* | 9/2010 | Keeling | ................ | G01N 33/004 702/24 |
| 2011/0068940 A1* | 3/2011 | Kim | ........................ | G01N 1/22 340/632 |

OTHER PUBLICATIONS

Whiticar, M. J. "Carbon and hydrogen isotope systematics of bacterial formation and oxidation of methane" Chemical Geology, (1999) 161: 291-314.
Whittaker, Steve "IEA GHG Weyburn-Midale CO2 Storage & Monitoring Project, In Regional Carbon Sequestration Partnerships Annual Review" Oct. 5th, 2010.
Whittaker, et al., "IEA GHG Weyburn CO2 Monitoring & Storage Project, Summary Report 2000-2004" In M. Wilson & M. Monea (Eds.), Proceedings of the 7th International Conference on Greenhouse Gas Control Technologies, Sep. 5-9, 2004, Vancouver, Canada (vol. III). Regina, SK: Petroleum Technology Research Centre.
Wolaver, et al. "Greensites and brownsites: Implications for CO2 sequestration characterization, risk assessment, and monitoring" International Journal of Greenhouse Gas Control, 19, 49-62 (2013).
Yang, et al. "Near-Surface Monitoring of Large-Volume CO2 Injection at Cranfield: Early Field Test of SECARB Phase III" SPE Journal, 18(3): 486-494, Jun. 2013.
Yang, et al. "Modeling CO2 Release Experiment in the Shallow Subsurface and Sensitivity Analysis" Environmental & Engineering Geoscience, 19(3): 207-220, Aug. 3, 2013.
Zhou, et al. "Noble gas tracing of groundwater/coalbed methane interaction in the San Juan Basin, USA" Geochimica et Cosmochimica Acta, 69, 5413-5428 (2005).
Romanak, et al. "Potential for a Process-based Monitoring Method above Geologic Carbon Storage Sites using Dissolved Gases in Freshwater Aquifers" Procedia Earth and Planetary Science, 7, 746-749 (2013).
European Patent Office (ISA), International Search Report and Written Opinion for PCT/US2014/044657 dated Sep. 10, 2014, 12 pp.
Beaubien, et al., "Monitoring of near-surface gas geochemistry at the Weyburn, Canada, CO2-EOR site, 2001-2011" International Journal of Greenhouse Gas Control, Available online Feb. 19, 2013, vol. 16, Supplement 1, pp. S236-S262.
Ecojustice "Site History, SW30-5-13-W2M Near Weyburn, Saskatchewan, Cameron and Jane Kerr" Calgary, AB: EcoJustice, Sep. 16, 2010.
Emberley, et al. "Monitoring of fluid—rock interaction and CO2 storage through produced fluid sampling at the Weyburn CO2-injection enhanced oil recovery site, Saskatchewan, Canada" Available online Apr. 22, 2005, Applied Geochemistry, 20, 1131-1157.
European Commission, Directive 2009/31/EC of the European Parliament and of the Council of Apr. 23, 2009 on the geological storage of carbon dioxide and amending Council Directive 85/337/EEC, European Parliament and Council Directives 2000/60/EC, 2001/80/EC, 2004/35/EC,2006/12/EC, 2008/1/EC and Regulation (EC) No. 1013/2006 Text with EEA relevance: Official Journal of the European Union L 140, May 6, 2009, p. 0114-0135.
Fredlund, et al. "Soil Mechanics for Unsaturated Soils"—Power Point Presentation. New York, NY: John Wiley & Sons, Inc. 1993.
Fryar, et al. "Nitrate reduction during ground-water recharge, Southern High Plains, Texas" 2000, Journal of Contaminant Hydrology 40, 335-363.
Furche, et al. "One year continuous vadose zone gas monitoring above an EGR test site" Geophysical Research Abstracts vol. 12, EGU2010-3095-1, 2010 7th EGU General Assembly, 2010.
Giammanco, et al. "Soil and fumaroles gases of Mount Etna: Geochemistry and relations with volcanic activity" 1998, Journal of Volcanology and Geothermal Research, 81, 297-310.
Gustavson, et al. "Depositional facies of the Miocene-Pliocene Ogallala Formation, northwestern Texas and eastern New Mexico" (1988) Geology, 16(3): 203-206.
Hackett, et al. "Geology and ground-water resources of the Gallatin Valley, Gallatin County, Montana, with a section on Surface-water, and a section on chemical quality of the water USGS Water Supply Paper: 1482" (1960).
Hanson, et al. "Separating root and soil microbial contributions to soil respiration: A review of methods and observations" 2000, Biogeochemistry, 48, 115-146.
Hovorka, S.D., "Quaternary evolution of playa lakes on the Southern High Plains—a case study from the Amarillo area, Texas" The University of Texas at Austin, Bureau of Economic Geology Report of Investigations No. 236, (1995), 52 p.
Kharaka, et al., "Changes in the chemistry of shallow groundwater related to the 2008 injection of CO2 at the ZERT field site, Bozeman, Montana" Environ Earth Sci (2010) 60:273-284.
Klusman, R.W. "Rate measurements and detection of gas microseepage to the atmosphere from an Enhanced Oil Recovery/sequestration project, Rangely, Colorado, USA" Applied Geochemistry, v. 18 (2003) pp. 1825-1838.
Klusman, R.W. "Computer modeling of methanotrophic oxidation of hydrocarbons in the unsaturated zone from an Enhanced Oil Recovery/sequestration project, Rangely, Colorado, USA" Applied Geochemistry, v. 18, (2003) pp. 1839-1852.
Klusman, R.W. "Detailed compositional analysis of gas seepage at the National Carbon Storage Test Site, Teapot Dome, Wyoming, USA" Applied Geochemistry, v. 21, (2006) pp. 1498-1521.
Klusman, R.W. "Comparison of surface and near-surface geochemical methods for detection of gas microseepage from carbon dioxide sequestration", International Journal of Greenhouse Gas Control 5, (2011) 1369-1392.
Lafleur, Paul "Geochemical Soil Gas Survey: A Site Investigation of SW30-5-13-W2M Weyburn Field, Saskatchewan" M. Saskatoon, SK: Petro-Find Geochem Ltd., Aug. 27, 2010, 27 pp.
Lafleur, Paul Geochemical Soil Gas Survey: A Site Investigation of SW30-5-13-W2M, Weyburn Field, Saskatchewan, Monitoring Project No. 2. Saskatoon, SK: Petro-Find Geochem Ltd., Mar. 16, 2011, 64 pp.
Mariotti, et al. "Experimental determination of nitrogen kinetic isotope fractionation: Some principles; illustration for the denitrification and nitrification processes" Plant and Soil 62(3): 413-430 (1981).
Marrin, Donn L. "Soil gas sampling and misinterpretation" Ground Water Monitoring Rev., vol. 8, p. 51-54. 1988.
Martin, et al. "Simultaneous determination of Argon and Nitrogen" Ground Water, 33, 781-785, Sep.-Oct. 1995.
Nicot, et al. "Shallow Subsurface Characterization of Gas Transport in a Playa Wetland", Gas phase dynamics of playa-wetlands: Journal of Environmental Engineering: 124: 1038-1046, (1998).
Ostendorf, et al., "Biodegradation of Hydrocarbon Vapors in the Unsaturated Zone" Water Resources Research, v.27, No. 4, p. 453-462, 1991.
Osterkamp, et al. "Playa-lake basins on the Southern High Plains of Texas and New Mexico: Part 1: Hydrologic, geomorphic, and geologic evidence for their development" GSA Bulletin, 99: 215-223, Aug. 1987.
Pataki, et al."The application and interpretation of Keeling plots in terrestrial carbon cycle research" Global Biogeochemical Cycles, 17, 22-1-22-14, 2003.

(56) References Cited

OTHER PUBLICATIONS

Petroleum Technology Research Centre "IEAGHG Weyburn-Midale CO2 Monitoring and Storage Project"—Response to a Soil Gas Study Performed by Petro-Find Geochem Ltd. Regina, SK: Petroleum Technology Research Centre, http://www.ptrc.ca/siteimages/WMP-Response-to-Petro-Find.pdf. Jan. 19, 2011.
Riding, et al. "The IEA Weyburn CO2 Monitoring and Storage Project: Final report of the European research team" Keyworth, Nottingham, UK: British Geological Survey. 2005.
Riding, et al. "Subsurface characterisation and geological monitoring of the CO2 injection operation at Weyburn, Saskatchewan, Canada" In Underground Gas Storage: Worldwide Experiences and Future Development in the UK and Europe, Special Publication 313, eds. D. J. Evans & R. A. Chadwick, 227-256. London: Geological Society. (2009).
Romanak, et al. "Process-Based Approach to Soil Gas Monitoring at Geologic Carbon Storage Sites" Geophysical Research Letters. 60 (2), 227-239, 2012.
Romanak, K.D. "Vadose-zone geochemistry of playa wetlands, High Plains, Texas" The University of Texas at Austin, Ph.D. dissertation, 273 p. (1997).
Saskatchewan Ministry of Energy and Resources, 2011, New Saskatchewan Stratigraphic Correlation Chart, internet resource, www.er.gov.sk.ca/stratchart. Revised Jan. 11, 2011.
Schoell, Martin "Multiple origins of methane in the earth" Chemical Geology, v. 71, p. 1-10.(1988).
Simpson, M. A. "Geology and Groundwater Resources of the Weyburn/Virden Area (62E/F), Saskatchewan" SRC Publication No. R-1210-3-E-93. Saskatoon, SK: Saskatchewan Research Council. (1993) 38 pp.
Smith, et al. "The Occurrence of Ethylene in Anaerobic Soil" Journal of Soil Science, 22, 430-443, 1971.
Spangler, et al. "A shallow subsurface controlled release facility in Bozeman, Montana, USA, for testing near surface CO2 detection techniques and transport models" Environ. Earth Sci. 6. 2010.
Strazisar, et al. "Near-surface monitoring for the ZERT shallow CO2 injection project" International Journal of Greenhouse Gas Control, 3(6): 736-744 (2009).
Striegl, et al. "Carbon dioxide retention and carbon exchange on vadose Quaternary sediments" Geochimica et Cosmochimica Acta, 54(8): 2277-2283 (1990).
Tilley, et al. "Gas maturity and alteration systematics across the Western Canada Sedimentary Basin from four mud gas isotope depth profiles" Organic Geochemistry, vol. 37, Issue 12, Dec. 2006, pp. 1857-1868 (Available online Nov. 21, 2006).
Trium Environmental Inc. "Site assessment Weyburn Unit SW30-5-13W2" www.cenovus.com, Nov. 2011.
U.S. Environmental Protection Agency "General technical support document for injection and geologic sequestration of carbon dioxide: subparts RR and UU" Greenhouse Gas Reporting Program, Office of Air & Radiation, Nov. 2010, 98 pp.
U.S. Environmental Protection Agency Mandatory Reporting of Greenhouse Gases: Injection and Geologic Sequestration of Carbon Dioxide; Final Rule, 75 FR 75060. Dec. 1, 2010, 31 pp.
Non-Final Office Action dated Aug. 10, 2016, for U.S. Appl. No. 14/318,087, 14 pages.
U.S. Appl. No. 14/318,087, filed Jun. 27, 2014, Notice of Allowance dated Jan. 23, 2017, all pages.
Patent Examination Report No. 1 dated Jun. 24, 2016, for Australian Patent Application No. 201430214, 3 pages.
Romanak, K.D., et al., Process-based approach to CO2 leakage detection by vadose zone gas monitoring at geologic CO2 storage sites, Geophysical Research Letters, vol. 39, L15405, Aug. 15, 2012, pp. 1-6.
Auxiliary Material for Process-based approach to CO2 leakage detection by vadose zone gas monitoring at geologic CO2 storage sites, Jul. 31, 2012, pp. 1-21.
International Preliminary Report on Patentability, PCT/US2014/044657, PCT, ISR dated Dec. 29, 2015, pp. 1-7.
Non-Final Office Action dated Mar. 3, 2016, for U.S. Appl. No. 14/318,087, 12 pages.
USEPA "A General Technical Support Document for Injection and Geologic Sequestration of Carbon Dioxide: Subparts RR and UU" Office of Air and Radiation U.S. Environmental Protection Agency, Nov. 2010, 98 pp.
USEPA "Mandatory Reporting of Greenhouse Gases: Injection and Geologic Sequestration of Carbon Dioxide; Final Rule" Federal Register, vol. 75, No. 230, Dec. 1, 2010, 31 pp.

* cited by examiner

PROCESS-BASED APPROACH FOR THE DETECTION OF CO2 INJECTATE LEAKAGE

CROSS-REFERENCE TO RELATED APPLICATIONS

This application claims priority to U.S. Provisional Application Ser. No. 61/840,234, filed Jun. 27, 2013, the entire contents of which are incorporated herein by reference.

STATEMENT OF FEDERALLY FUNDED RESEARCH

This invention was made with U.S. Government support by the U.S. Department of Energy through the Office of the Governor of Texas (contract DE-FG04-90AL65847) and the National Energy Technology Laboratory (contract DE FG26-05NT42590) through the Southeast Regional Carbon Sequestration Partnership. The government has certain rights in this invention.

TECHNICAL FIELD OF THE INVENTION

The present invention relates in general to the field of gas detection, and more particularly, to a novel process-based approach for the detection of injectate leakage from deep reservoirs.

BACKGROUND OF THE INVENTION

Without limiting the scope of the invention, its background is described in connection with detecting gas in the vadose zone.

Measurement, monitoring and verification (MMV) will be required at geologic carbon storage (GCS) sites to document that storage effectively retains $CO_2$ in the subsurface [European Commission, 2009: US EPA, 2010a, b]. MMV can utilize many techniques deployed at a range of depths from the storage reservoir to the atmosphere, however techniques that monitor leakage through the near surface vadose zone are valuable because: (1) the vadose zone is the interface between subsurface storage and release to atmosphere; (2) gases moving through the shallow subsurface are easily and cheaply monitored; and (3) vadose zone monitoring can directly address concerns of landowners living above GCS sites [Sherk et al., 2011].

The most studied and currently widely accepted approach for vadose zone gas monitoring above GCS sites directly measures $CO_2$ concentrations either by extracting vadose zone gas through hollow push probes or by measuring $CO_2$ surface flux with accumulation chambers. Measurements are made in a grid pattern or in areas of concern, such as faults, fractures, or plugged and abandoned wells [Riding and Rochelle, 2009: Strazisar et al., 2009: Furche et al., 2010]. A minimum of 1 year of background concentration measurements is required prior to $CO_2$ injection to document natural seasonal ranges in vadose zone $CO_2$ apart from leakage. If $CO_2$ concentrations statistically exceed the background range during the lifetime of a GCS project, a storage formation release may be indicated. This approach is herein referred to as a "$CO_2$ concentration-based" approach.

A $CO_2$ concentration-based approach has several drawbacks: (1) high variability of $CO_2$ generated in situ could mask a moderate leakage signal; (2) 1 year of background characterization cannot account for $CO_2$ variability from climatic, land use, and ecosystem variations over the lifetime (tens to hundreds of years) of a storage project; (3) background measurements require a long lead time potentially hindering a project's progress; and (4) background $CO_2$ cannot be measured across all potential small diameter leak points within the area of review: therefore, if concerns arise in an area lacking local background measurements, no baseline data exist with which to compare monitored $CO_2$ concentrations.

SUMMARY OF THE INVENTION

In one embodiment, the present invention includes a method of distinguishing between a natural source of deep gas and gas leaking from a $CO_2$ storage reservoir at a near surface formation comprising: obtaining one or more surface or near surface geological samples; measuring a $CO_2$, an $O_2$, a $CH_4$, and an $N_2$ level from the surface or near surface geological sample; determining the water vapor content at or above the surface or near surface geological samples; normalizing the gas mixture of the $CO_2$, the $O_2$, the $CH_4$, the $N_2$ and the water vapor content to 100% by volume or 1 atmospheric total pressure; determining: a ratio of $CO_2$ versus $N_2$ to distinguish whether $CO_2$ is being removed from the near surface formation or $CO_2$ is added from an exogenous deep leakage input; and a ratio of $CO_2$ to $N_2$, wherein if the ratio is greater than that produced by a natural source of deep gas $CO_2$ or deep gas methane oxidizing to $CO_2$, the ratio is indicative of gas leaking from a $CO_2$ storage reservoir; wherein the presence of at least one of (1) or (2) is indicative of gas leaking from a $CO_2$ storage reservoir. In one aspect, the method further comprises determining the ratio of $O_2$ to $CO_2$, wherein if the amount of $CO_2$ is greater than $CO_2$ from biological respiration and $CO_2$ from the oxidation of $CH_4$ in the near surface formation in relation to the level of $N_2$ there is gas leaking from a $CO_2$ storage reservoir. In another aspect, the presence of a deep gas source of carbon is indicated if the water saturated atmospheric value of $N_2$ is less than 76.4%. In another aspect, if the level of $O_2$ is determined by gas chromatography without separation of $O_2$ and Argon peaks, the method further comprises subtracting the level of Argon from the level of $O_2$ to determine the actual level of $O_2$. In another aspect, the amount of Argon is calculated equal to $1/63 \times N_2$ concentration. In another aspect, the water vapor is saturated. In another aspect, the amount of water vapor is 2.1 to 2.4%, 2.2 to 2.35%, or 2.3%. In another aspect, the deep $CO_2$ gas versus $CO_2$ from biological respiration is in the near surface formation if the level of $N_2$ is below 76.4% in a water vapor saturated vadose zone environment. In another aspect if the vadose zone environment is dry, the presence of deep gas may be indicated if $N_2$ above 78%. In another aspect, an $N_2/O_2$ ratio greater than air indicates influx of air and/or $O_2$ consumption. In another aspect, the water vapor content is measured or estimated. In another aspect, the samples are collected in a sealed container and later analyzed in a laboratory.

Another embodiment of the present invention include a method of distinguishing between a natural source of deep gas and gas leaking from a $CO_2$ storage reservoir at a near surface formation comprising: obtaining one or more surface or near surface geological samples; measuring a $CO_2$, an $O_2$, a $CH_4$, and an $N_2$ level from the surface or near surface geological sample; determining the water vapor content at or above the surface or near surface geological samples; normalizing the gas mixture of the $CO_2$, the $O_2$, the $CH_4$, the $N_2$ and the water vapor content to 100% by volume or 1 atmospheric total pressure; determining: (1) a ratio of $O_2$ to $CO_2$, wherein if the amount of $CO_2$ is greater than $CO_2$ from biological respiration and $CO_2$ from the oxidation of $CH_4$ in the near surface formation in relation to the level of $N_2$ there is gas leaking from a $CO_2$ storage reservoir; (2) a ratio of $CO_2$ versus $N_2$ to distinguish whether $CO_2$ is being removed from the near surface formation or $CO_2$ is added from an exogenous deep leakage input; and (3) a ratio of $CO_2$ to $N_2$, wherein if the ratio is greater than that produced by a natural source of deep gas $CO_2$ or deep gas methane oxidizing to $CO_2$, the ratio is indicative of gas leaking from a $CO_2$ storage reservoir; wherein the presence of two ratios selected from (1), (2), or (3), is indicative of gas leaking from a $CO_2$ storage reservoir. In one aspect, if the level of $O_2$ is determined by gas chromatography, the method further comprises calculating the level of Argon in the sample and subtracting the level of Argon from the level of $O_2$ to determine the actual level of $O_2$. In another aspect, the presence of a deep gas source of carbon is indicated if the water saturated atmospheric value of $N_2$ is less than 76.4%. In another aspect, if the level of $O_2$ is determined by gas chromatography without separation of $O_2$ and Argon peaks, the method further comprises subtracting the level of Argon from the level of $O_2$ to determine the actual level of $O_2$. In another aspect, the amount of Argon is calculated equal to $1/63 \times N_2$ concentration. In another aspect, the water vapor is saturated. In another aspect, the amount of water vapor is 2.1 to 2.4%, 2.2 to 2.35%, or 2.3%. In another aspect, the deep $CO_2$ gas versus $CO_2$ from biological respiration is in the near surface formation if the level of $N_2$ is below 76.4%. In another aspect, an $N_2/O_2$ ratio greater than air indicates influx of air and $O_2$ consumption. In another aspect, the water vapor content is measured or estimated. In another aspect, the samples are collected in a sealed container and later analyzed in a laboratory.

In yet another embodiment, the present invention includes a method of distinguishing between a natural source of deep gas and gas leaking from a $CO_2$ storage reservoir at a near surface formation comprising: obtaining one or more surface or near surface geological samples; measuring a $CO_2$, an $O_2$, a $CH_4$, and an $N_2$ level from the surface or near surface geological sample; determining the water vapor content at or above the surface or near surface geological samples; normalizing the gas mixture of the $CO_2$, the $O_2$, the $CH_4$, the $N_2$ and the water vapor content to 100% by volume or 1 atmospheric total pressure; determining: (1) a ratio of $O_2$ to $CO_2$, wherein if the amount of $CO_2$ is greater than $CO_2$ from biological respiration and $CO_2$ from the oxidation of $CH_4$ in the near surface formation in relation to the level of $N_2$ there is gas leaking from a $CO_2$ storage reservoir; (2) a ratio of $CO_2$ versus $N_2$ to distinguish whether $CO_2$ is being removed from the near surface formation or $CO_2$ is added from an exogenous deep leakage input; and (3) a ratio of $CO_2$ to $N_2$, wherein if the ratio is greater than that produced by a natural source of deep gas $CO_2$ or deep gas methane oxidizing to $CO_2$, the ratio is indicative of gas leaking from a $CO_2$ storage reservoir; wherein the presence of all three is indicative of gas leaking from a $CO_2$ storage reservoir.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
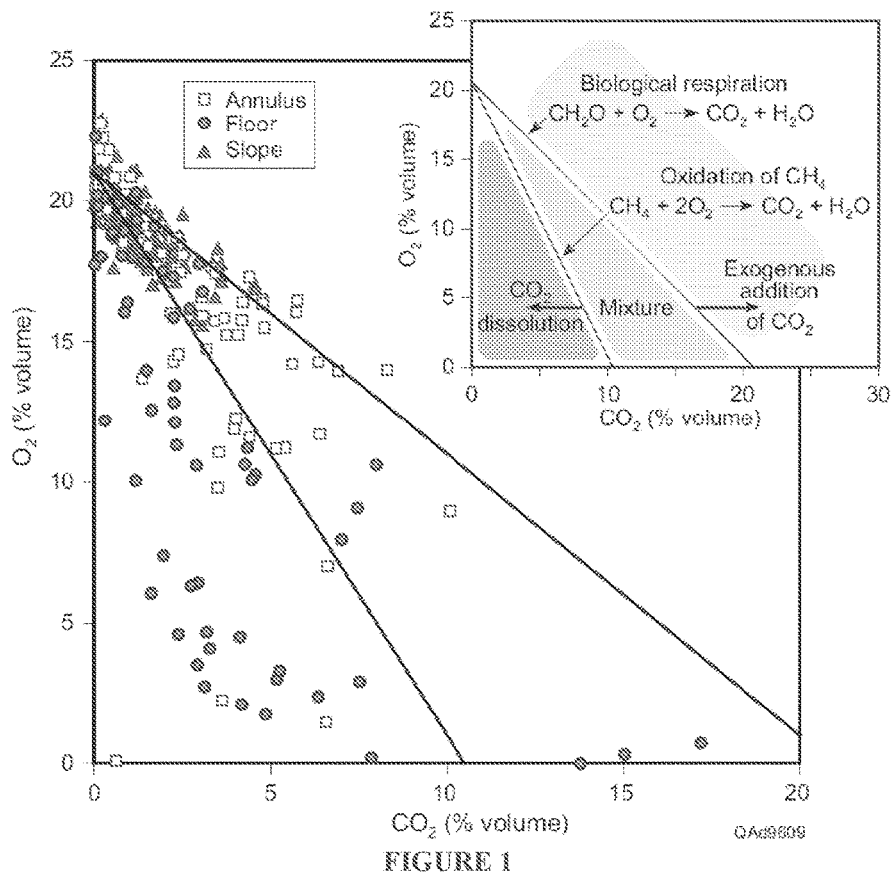
FIG. 1 is a graph that shows soil gas data from a natural $CO_2$-rich playa site shown with general soil gas trends for common background processes of biologic respiration and methane oxidation (lines inside graph). Possible deviations are shown (inset). Gas compositions that plot below both the biological respiration and $CH_4$ oxidation lines indicate $CO_2$ dissolution and reaction with soil carbonate. Data representing a $CO_2$ leak from depth into the vadose zone would plot above these trend lines in the exogenous gas input field.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A critical issue for geologic carbon sequestration is the ability to detect $CO_2$ leakage in the vadose zone. The present inventors demonstrate herein a new process-based approach to identify $CO_2$ that has leaked from deep geologic storage reservoirs into the shallow subsurface. Whereas current $CO_2$ concentration-based methods require years of background measurements to quantify variability of natural vadose zone $CO_2$, this new approach examines chemical relationships between vadose zone $N_2$, $O_2$, $CO_2$, and $CH_4$ to promptly distinguish a leakage signal from background $CO_2$. The method uses sequential inspection (1) $O_2$ versus $CO_2$ to distinguish in-situ vadose zone background processes (biologic respiration, methane oxidation, and $CO_2$ dissolution) from exogenous deep leakage input, (2) $CO_2$ versus $N_2$ to further distinguish dissolution of $CO_2$ from exogenous deep leakage input, and (3) $CO_2$ versus $N_2/O_2$ to assess the degree of atmospheric mixing/dilution occurring in the system. The approach was developed at a natural $CO_2$-rich analog site and successfully applied at a $CO_2$-enhanced oil recovery operation where deep gases migrated into the vadose zone. The ability to identify $CO_2$ leakage into the vadose zone without the need for background measurements could decrease uncertainty in leakage detection and expedite implementation of future geologic $CO_2$ storage projects.

To address the problem of separating signal (leaked) from background (in situ generated) $CO_2$ in the vadose zone, the present invention includes, for the first time, a powerful, yet simple geochemical approach to GCS leakage monitoring that does not require background monitoring. Instead, relationships among major fixed gases ($CO_2$, $N_2$, $O_2$, $CH_4$) are used to identify processes that produce and consume vadose zone $CO_2$. It was found herein that the major in situ vadose zone processes in this analysis can distinguish: biologic respiration, $CH_4$ oxidation, dissolution of $CO_2$ and reaction with soil carbonate, and atmospheric mixing.

Vadose zone processes. In the absence of carbon cycling processes, vadose zone gases are dominated by the atmosphere (in dry air, 78% $N_2$, 21% $O_2$, 0.039% $CO_2$, 1.8 ppm $CH_4$), which invades the subsurface via barometric pumping and diffusion. Root and microbial respiration in the vadose zone increases $CO_2$ and decreases $O_2$ relative to the atmosphere [Hanson et al., 2000] and is affected by temperature, soil moisture content, nutrient availability and oxygen supply which vary on diurnal, seasonal, and longer-term climatic timescales [e.g. Luo and Zhou, 2006]. Microbial respiration commonly produces $CO_2$ wherever organic matter, $O_2$, and soil moisture coexist, but when $O_2$ and other electron acceptors such as nitrate and sulfate are depleted, $CH_4$ is eventually produced [Konhauser, 2006]. If $CH_4$ migrates into oxic zones or if environmental change allows $O_2$ influx, $CH_4$ is oxidized to $CO_2$ [Whalen et al., 1990], potentially mimicking a storage formation leak signal. $CH_4$ oxidation is therefore important to identify wherever in situ $CH_4$ is produced or above oil and gas fields where $CH_4$ may seep from deep reservoirs into the vadose zone over geologic time. Soil gas $CO_2$ may be consumed by dissolution into infiltrating water and reaction with carbonate mineral phases [Stiegl and Armstrong, 1990], forming a significant $CO_2$ sink. Vadose zone gas concentrations are also affected by invasion of atmosphere into the subsurface [Osterkamp and Wood, 1987], which can be induced by barometric pressure changes but may also result from pressure gradients caused by dissolution of gas into recharging water [Smith and Arah, 1991: Romanak, 1997: Nicot and Bennett, 1998].

Beginning with atmospheric gas concentrations, vadose zone processes alter soil gas geochemistry in predictable ways on the basis of either reaction stoichiometry or decoupling of gas components. Gas concentrations are measured in percent (volume or molar); therefore, any non-reactive addition or subtraction of a gas component will, by definition, dilute or concentrate, respectively, all other gases in similar proportions. The fixed composition of atmosphere, which dominates the vadose zone in the absence of background or leakage processes, provides the starting point from which to assess reactions. $N_2$ is a good measure of dilution and/or enrichment of a gas mixture owing to its abundance in air and non-reactivity which is compromised only in extreme cases of denitrification [Fryar et al., 2000]. Denitrification can be identified by $N_2$ that is depleted in $^{15}N$ relative to atmosphere ($\delta^{15}N=0$‰) [Mariotti et al., 1981], or by $Ar/N_2$ that is significantly less than 0.0119 [Martin et al, 1995].

The process in soils posing the greatest challenge to $CO_2$ concentration based monitoring is $CO_2$ production by oxidation of organic matter during aerobic microbial respiration. This process is represented as:

$$CH_2O + O_2 \rightarrow CO_2 + H_2O \qquad (1)$$

where $O_2$ consumption and $CO_2$ production result in a predictable trend (slope of −2) originating from atmospheric concentrations) on a graph of $CO_2$ versus $O_2$ (FIG. 1). During methane oxidation, $$CH_4 + 2O_2 \rightarrow CO_2 + 2H_2O \qquad (2)$$

$O_2$ consumption and $CO_2$ production produce a trend with a slope of −0.5 on the same graph. $CO_2$ values higher than expected from corresponding $O_2$ values signal an exogenous $CO_2$ source, indicating a potential leak, and $CO_2$ values lower than expected from corresponding $O_2$ values signal a $CO_2$ sink.

EXAMPLE 1

Novel Process-based Leakage Detection

Study sites. The process-based leakage detection approach was developed at a natural $CO_2$-rich ephemeral playa lake in west Texas, USA. Here, known vadose zone processes were coupled with their corresponding soil gas signatures. This information was then successfully applied at an oil field in Mississippi at the site of a plugged and abandoned well to identify anomalous near-surface $CO_2$ and $CH_4$ soil gas signals.

Playa Natural Analog. The playa lakes of west Texas are broad, gently sloping circular basins (~1 to 2 km in diameter) that accumulate and transmit surface runoff through a thick (~60 m) vadose zone. Geomorphic areas associated with playas, which include: slope, annulus, and floor, systematically differ in water flux, organic carbon content, and inorganic soil carbonate, creating spatial variability in the main factors that affect natural vadose zone CO2 production and consumption [Osterkamp and Wood, 1987; Romanak, 1997]. These systematic differences provide an opportunity to link various natural CO2 cycling processes to their vadose zone soil gas signatures. The low-angle playa slope defines the outer edge of the playa basin and transmits storm runoff onto playa floors [Gustayson and Winkler, 1988]. The annulus, a sort of "bathtub ring" defined by a break in slope around the lake's shoreline, transmits water through silty sediments only during high water levels [Hovorka, 1996; Scanlon et al., 1997]. Organic-rich clays and silty clay loams of the flat playa floor pond water before transmitting it along shrink-swell fractures and root tubules through clay deposits [Hovorka, 1996: Scanlon et al., 1997]. Beneath playa floors, dissolved organic carbon is microbially oxidized to produce CO2 which dissolves soil carbonate to create piping and secondary pores as large as 7 mm in diameter (Osterkamp and Wood, 1987).

The specific playa studied herein is located at 35° 25' 2.2" N, 101° 30' 8.4" W, with a diameter of 0.8 km. Soil gas collected during 10 sampling trips between August 1992 and May 1995 was analyzed for $CO_2$, $O_2$, $N_2$, $CH_4$, $\delta^{13}C$ of $CO_2$, and $^{15}N$ of $N_2$ from 23 stations containing 54 semi-permanent soil gas wells at depths ranging from 0.6 to 13.7 m. Stations were installed along radial transects extending through slope, annulus and floor areas to identify variations in soil gas concentrations under varying environmental conditions.

Industrial Oil Field Site. Methods applied at the playa study were applied at an area named the P-site at the Cranfield oil field 18 km east of Natchez Miss., USA (31° 34' 11.8" N, 91° 9' 27.4" W) where oil production from the Tuscaloosa Formation (3050 m depth) began in 1944 [Hines, 1950]. Depletion of the field by 1966 was followed by plugging and abandonment of approximately 100 wells in the 31 $km^2$ oil field. $CO_2$-enhanced oil recovery (EOR) began in 2008 by Denbury Resources Inc.

Vadose zone monitoring at the P-site began before local $CO_2$ injection. At the site, 13 multi-depth gas sampling stations with a total of 39 gas wells as deep as 3 m were installed in various locations around an 1124 $m^2$ gravel pad. One transect extends from an open pit used during 1950s oil production, across the gravel pad near a plugged and abandoned well, and out onto a grassy clearing defined as a background location. Data from portions of this major transect collected over a one-year period.

At both study sites, semi-permanent gas wells were used to sample gas from different depths within the vadose zone (see Well Station Construction, below). This installation type provides: (1) depth profiles of subsurface gas distribution, (2) potential for repeat sampling with exact spatial matching, and (3) sediment samples for assessment of parameters important to reactive transport modeling, soil contamination, or soil/water interactions. Boreholes were as deep as 14 m and well placement was targeted to areas of concern identified through reconnaissance sampling using a standard push probe.

Well Station Construction. Semi-permanent soil gas sampling stations were comprised of multiple sampling tubes (0.64-cm copper tubing at the playa and 0.32-cm stainless steel tubing at Cranfield) installed at depths of interest within each 5-cm diameter borehole. [Note: Wells can generally be installed in any size borehole that will accommodate the number of wells desired however larger diameter holes require more material for back-filling. Generally 5 cm diameter boreholes are desirable and will accommodate up to four wells]. Before drilling, all underground infrastructures were identified to avoid hitting gas or electrical lines. At the down-hole end of the Cranfield gas sampling wells, 152 mm stainless steel mesh screens (Geoprobe 15-cm vapor implants) were connected with Swagelok gas-tight fittings. Screens were set in 20-30 cm of quartz sand. The borehole was then backfilled with wetted bentonite clay chips to isolate the sampling interval until the next sampling level was reached. The process was repeated until all gas sampling wells were set in sand pack and their sampling intervals isolated with bentonite. Each gas sampling well was carefully labeled with its depth and topped with either a rubber tip (playa) or a noflow Swagelok quick connect stem (SS-QM2-D-200) that stops air from entering the tube until it is joined to the sampling hose with a quick connect body (SS-QM2-B-200) (Cranfield). All gas well tubing was cut at similar heights above ground surface (~0.3 to 0.5 meters). When the borehole was filled to within 0.5 m of ground surface, a PVC protector pipe was installed over the sampling tubes, inserted into the remaining space within the borehole and secured by adding wetted bentonite around the annulus to hold it in place. The pipe was capped and labeled and protected the gas sampling wells from environmental damage.

Field GC Analysis. A Masterflex E/S portable peristaltic pump was used to draw soil-gas from wells at a flow rate of approximately 50 to 100 cc/min and deliver the sample to the gas chromatograph (GC) through tygon tubing directly plumbed to the inlet of the GC sample loop. During sampling, either an in-line pressure gauge for monitoring well pressure or a flow meter for monitoring flow rate were used to verify that no vacuum pressure developed risking dilution with ambient air or cross contamination from other sampling depths. Prior to GC analysis, the sample line to the well was purged for a sufficient time to void 2-3 well/sample line volumes. Sampling at each well continued until three runs with stable concentrations within ±10% relative difference) for each analyte were obtained. The GC was calibrated using air and certified low and high standard gas mixtures (Scot brand) spanning expected nominal concentration ranges before, during, and after each day's sampling. The precision for both detectors is ±2%.

On-site analysis of major gas compounds ($CO_2$, $O_2$, $N_2$, and $CH_4$) was accomplished at both sites using a portable gas chromatograph (SRI 8610) fixed with a CTR2 binary column (Porapak Q and molecular sieve), thermal conductivity (TCD) and flame ionization (FID) detectors, hydrogen carrier gas at various flow rates (35-46 mls/min), and isothermal temperatures of 30-45° C. A methanizer on the FID brought detection limits for CO2 down to atmospheric concentrations. This chromatographic method does not separate argon (Ar) from $O_2$, therefore, Ar was estimated at 1/83 of $N_2$ and subtracted from the $O_2$ measurement which is acceptable when denitrification is insignificant $N_2$ [Smith and Arah, 1991]. As 2.2% water vapor representing saturated water vapor pressure was added to all All sample measurements were normalized to 100% for comparison purposes due to slight differences in the inlet pressures at the GC sample loop from variations in pumping rates.

Laboratory Analysis. Gas samples for $\delta_{13}C$ and $\delta_{15}N$ were collected in stainless steel gas cylinders with Swagelok fittings at the playa site and in pre-evacuated Cali 5-bond gas bags at Cranfield. Carbon isotopes for the playa study were analyzed by mass spectrometer at Coastal Isotope Laboratories in Austin Tex. ($\delta_{13}C$ relative to PDB standard with a precision of ±0.2%). $\delta_{15}N$ was measured by mass spectrometer at the Department of Environmental Sciences at the University of Virginia with atmospheric nitrogen as the standard and precision ±0.15%). $\delta_{13}C$ of $CO_2$ and $CH_4$ and $\delta D$ of $CH_4$ at Cranfield were collected in preevacuated Cali 5-bond gas bags and analyzed at Isotech Laboratories (Champaign, Ill.) using a GC-CIRMS system. This method employs a GC combustion unit interfaced with a mass spectrometer (Delta V Plus or Delta Plus Advantage). Samples are injected into the GC split/splitless injector and are separated by the GC column. Each individual hydrocarbon ($CH_4$) component is combusted and the resultant $CO_2$ is introduced directly into the mass spectrometer. Hydrogen isotopic values for methane are completed using the same system, but the gas is channeled through a high-temperature pyrolysis furnace instead of through the combustion furnace. The pyrolysis furnace converts methane into $H_2$ and carbon, and the $H_2$ gas is introduced directly into the mass spectrometer. Nitrogen isotopic data for elemental nitrogen ($N_2$) is generated using the same system. For measurement of isotopes of $CO_2$, the gas does not pass through a combustion furnace but is channeled directly from the GC outlet to the collection trap. Stated precision for $\delta_{13}C$ is ±0.3% and for $\delta D$ ±2.0%.

Major gas compounds ($CO_2$, $O_2$, $N_2$, and $CH_4$) were analyzed on-site at both study areas using a portable gas chromatograph. Samples were also collected for laboratory isotope analyses including $\delta^{13}C$ of $CO_2$ and $CH_4$, $\delta D$ of $CH_4$, and $^{15}N$ of $N_2$. Playa samples were collected in stainless steel gas cylinders with Swagelok fittings and analyzed either by mass spectrometer at Coastal Laboratories, Austin, Tex. ($\delta^{13}C$ of $CO_2$) or at the University of Virginia ($\delta^{15}N$ of $N_2$). Isotopes of Cranfield gases ($\delta^{13}C$ of $CO_2$ and $CH_4$, and $\delta D$ of $CH_4$) were collected in Cali-5-bond bags and analyzed at Isotech Laboratories, Champaign, Ill. by mass spectrometer.

Natural Analog Playa Site. In the playa, maximum concentrations of $CO_2$ (slope: 5.0%, annulus: 10.5%, floor: 17.2%) and $CH_4$ (slope: 0%, annulus: 2.2%, floor: 0.9%), coupled with minimum $O_2$ (slope: 15.6%, annulus: 0.1%, and floor 0.0%) indicate that microbial $CO_2$ and $CH_4$ production is relatively low in the slope, where organic carbon content and water flux is low, and high in the floor, where organic carbon content and water flux is high. The annulus is a transitional zone, behaving like the slope when dry and the floor when high water levels allow water infiltration through annulus sediments.

Figure 2:
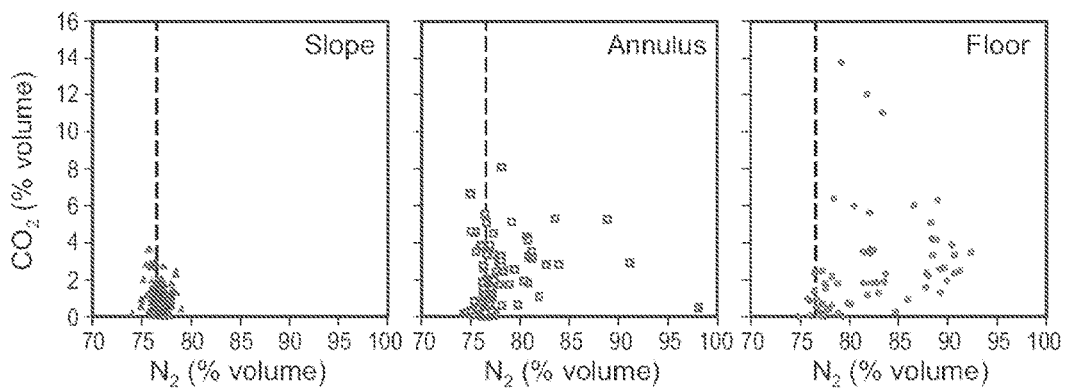
FIG. 2 shows three graphs that show a comparison of trends in $CO_2$ versus $N_2$ for various natural playa zones (slope, annulus, floor). Dashed line indicates atmospheric $N_2$ concentration in water vapor saturated soils (76.4%). Enrichment of $N_2$ concentrations above atmospheric values (samples to the right of the dashed line) indicates that the background process of $CO_2$ dissolution into recharging groundwater has occurred. If samples lie significantly to the left of the dashed line, exogenous gas input from deep reservoir leakage may be indicated.
Figure 6:
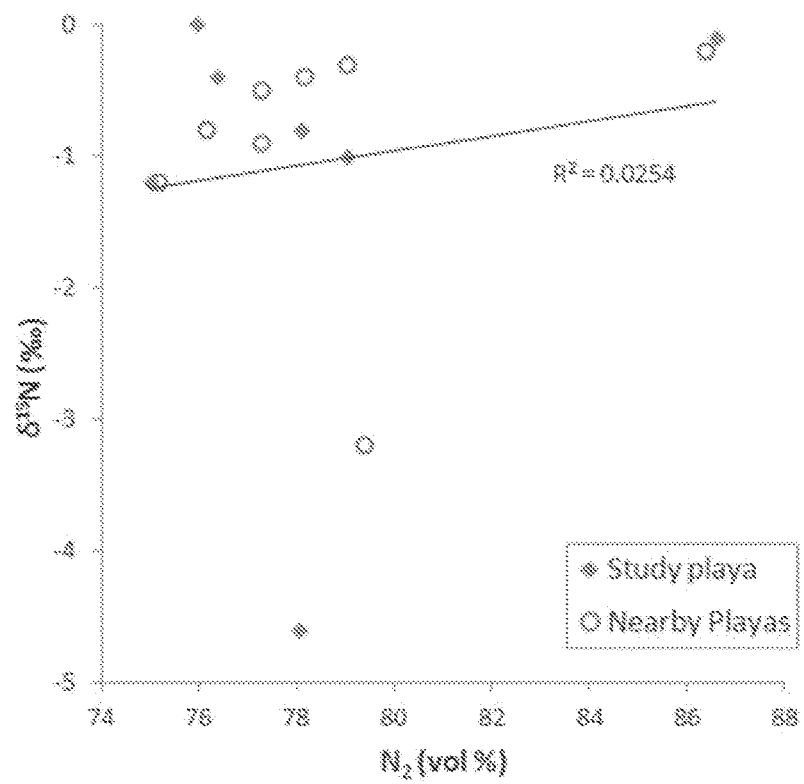
FIG. 6 is a graph of $\delta^{15}N$ versus $N_2$ concentrations for the study playa and for two other nearby playas in west Texas. Location information on additional playas as well as a discussion about nitrogen in playas can be found in Fryar et al. (2000). The data indicate little co-variation between the two parameters suggesting that although denitrification does occur, it is not significantly affecting nitrogen concentrations beneath playas.

Gas compositions from the slope and annulus, and a few from the floor, cluster between trends for microbial respiration and $CH_4$ oxidation on a graph of $CO_2$ versus $O_2$ with some analytical scatter (FIG. 1). Many samples from the playa floor lie below both trend lines indicating a loss of $CO_2$ from the gas phase. Samples that indicate this loss of $CO_2$ (most gas compositions from the floor and some from the annulus) generally also exhibit $N_2$ values enriched above atmospheric values (FIG. 2). Nitrogen isotope ratios of gas sampled from three area playas show insignificant denitrification, indicated by a lack of covariation between $N_2$ and $^{15}N(R^2=0.0254)$ for 15 samples (FIG. 6). Comparison of $N_2$ and $CO_2$ concentrations from each playa zone (FIG. 2) shows the following relationships: (1) $N_2$ values in the slope (74.0-79.0%) resemble those of the atmosphere, (2) $N_2$ values in the floor (74.8-92.4%) are predominantly enriched relative to the atmosphere, and (3) $N_2$ signatures in the annulus (74.3-98.1%) are mixed, depending on whether the annulus was wet and undergoing infiltration or dry.

$N_2$ concentrations enriched relative to the atmosphere suggest the dissolution of $CO_2$ into recharging groundwater enhanced by concurrent dissolution of soil carbonate. The loss of $CO_2$ from the gas phase enriches the percent concentration of $N_2$ above atmospheric values. $N_2$ enrichment is augmented by advection of the atmosphere into soil pores driven by the pressure differential created from loss of $CO_2$ gas [Smith and Arah, 1991: Nicot and Bennett, 1998].

Figure 3:
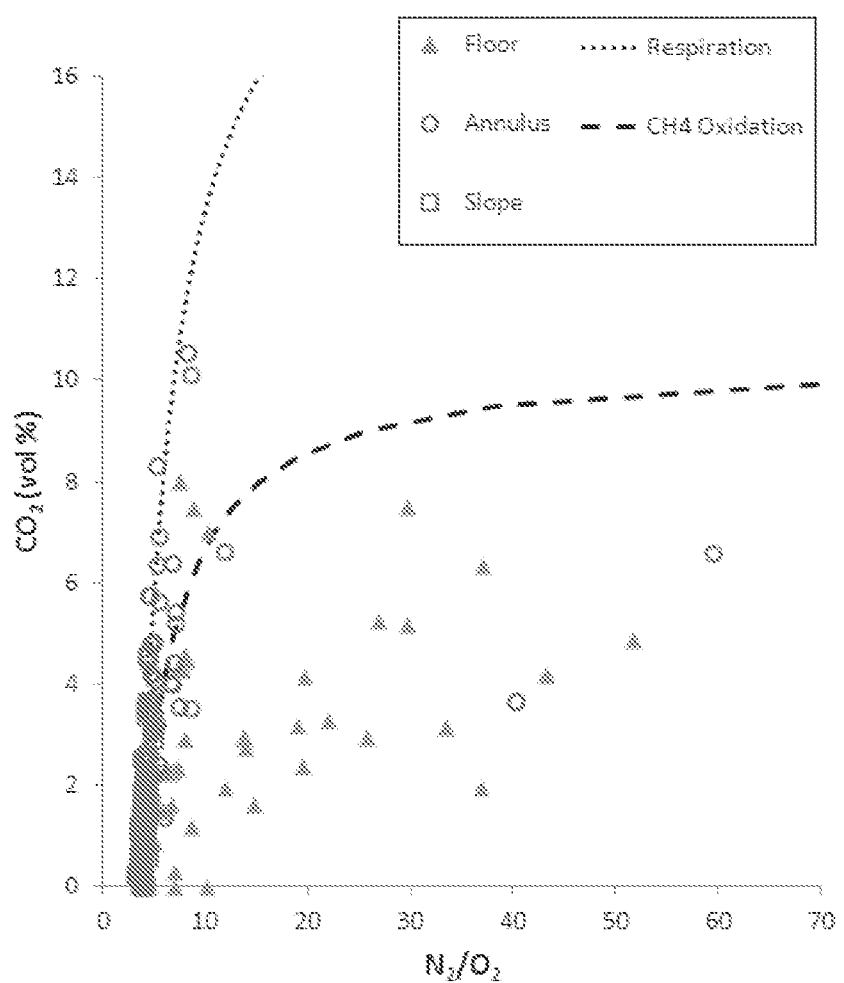
FIG. 3 is a graph that shows gas composition relationships of $CO_2$ versus $N_2/O_2$ for the playa study site. Trends for $O_2$ consumption during biologic respiration and $CH_4$ oxidation are shown. These relationships distinguish the amount of oxygen input and utilization. In a natural system with no exogenous input from depth, gases that undergo $CO_2$ dissolution and mixing with air will migrate to lower $CO_2$ concentrations and higher $N_2/O_2$ ratios.

Oxygen consumption during $CH_4$ oxidation, and to a lesser degree from microbial respiration, is identified by $N_2/O_2$ above the atmospheric ratio of 3.8 (FIG. 3), in the absence of significant denitrification. Whereas both atmospheric mixing and $CO_2$ dissolution retain a 3.8 ratio, $O_2$ consumption increases this ratio. At the playa, $O_2$ consumption from microbial respiration increases $N_2/O_2$ to as high as 10, whereas $CH_4$ oxidation coupled with air influx increases this ratio to as high as 60 (FIG. 3). $N_2/O_2$ is therefore an indicator of the magnitude of oxygen influx and consumption which can be an indicator of $CH_4$ oxidation and discriminates microbial respiration and carbonate dissolution from $CH_4$ oxidation which is an especially important distinction in hydrocarbon fields where oxidized $CH_4$ seepage could be mistaken for a $CO_2$ leak.

Figure 5:
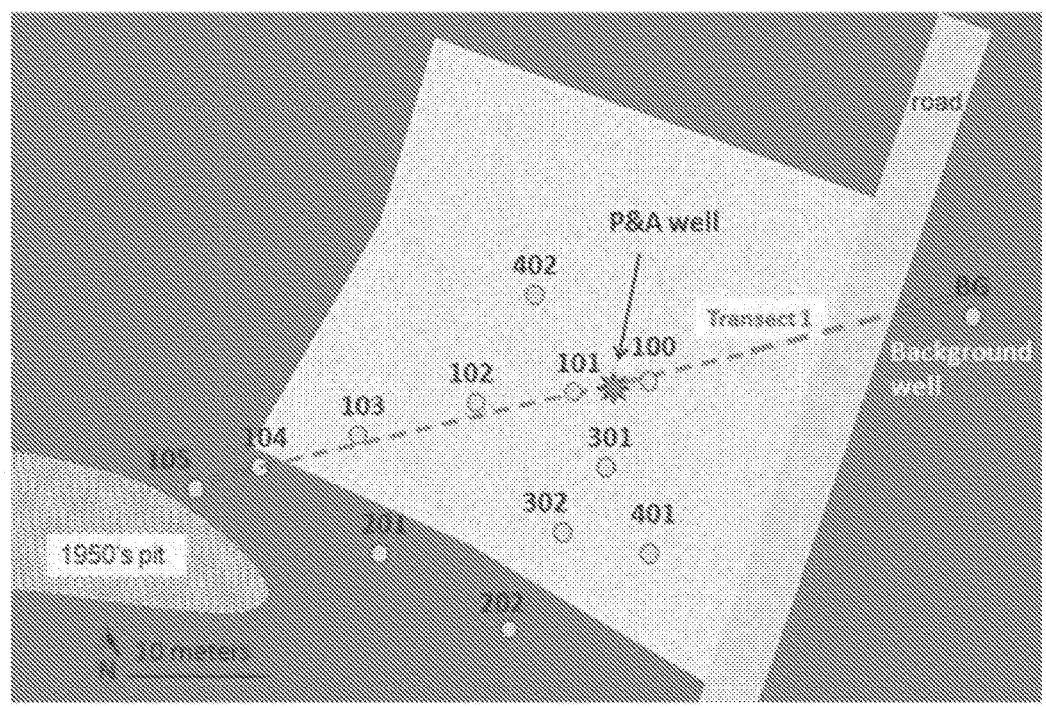
FIG. 5 is a map showing gas sampling locations at the p-site, Cranfield oilfield. Data are reported for stations BG, 100, 101, 103. Additional drilling sites are labeled 102, 104, 105, 201, 202, 301, 302, 401 and 402. The main transect is indicated by the hashed line.
Figure 7:
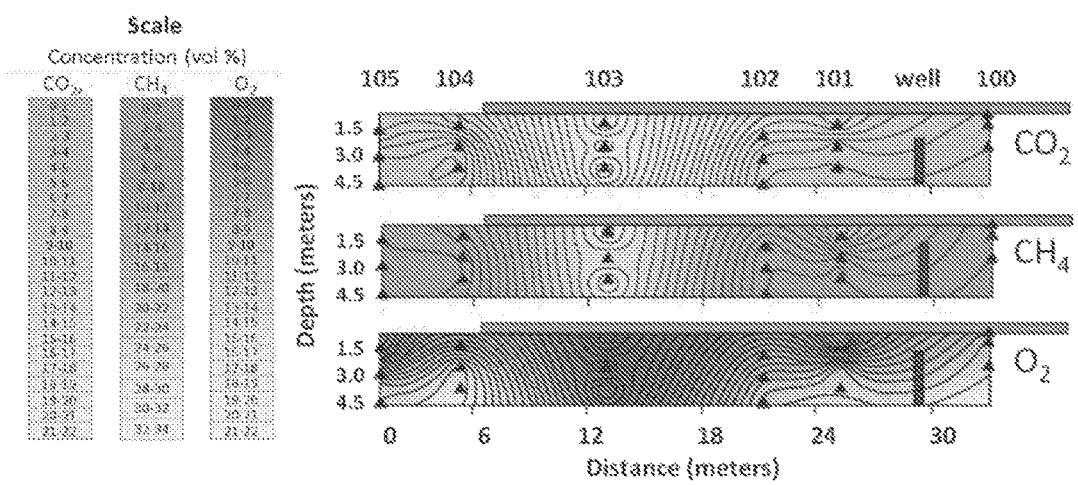
FIG. 7 shows a cross section of $CO_2$ (≤21.4%), $CH_4$ (≤33.3%), and $O_2$ (0-21%) gas concentrations along the main gas sampling transect at the Cranfield oil field near the soil gas anomaly (centered at 103), see FIG. 5 for numbered locations). Light colors indicate high concentrations; dark colors indicate low concentrations (scale at left). The cross section is presented to show the general distribution of gases in the subsurface. High concentrations of $CO_2$ and $CH_4$ correspond with low $O_2$. Gas diffusion gradients favor lateral migration near the anomaly and vertical migration away from the anomaly. $O_2$ appears to invade the subsurface at some distance from the anomaly epicenter migrating laterally at depth.
Figure 8:
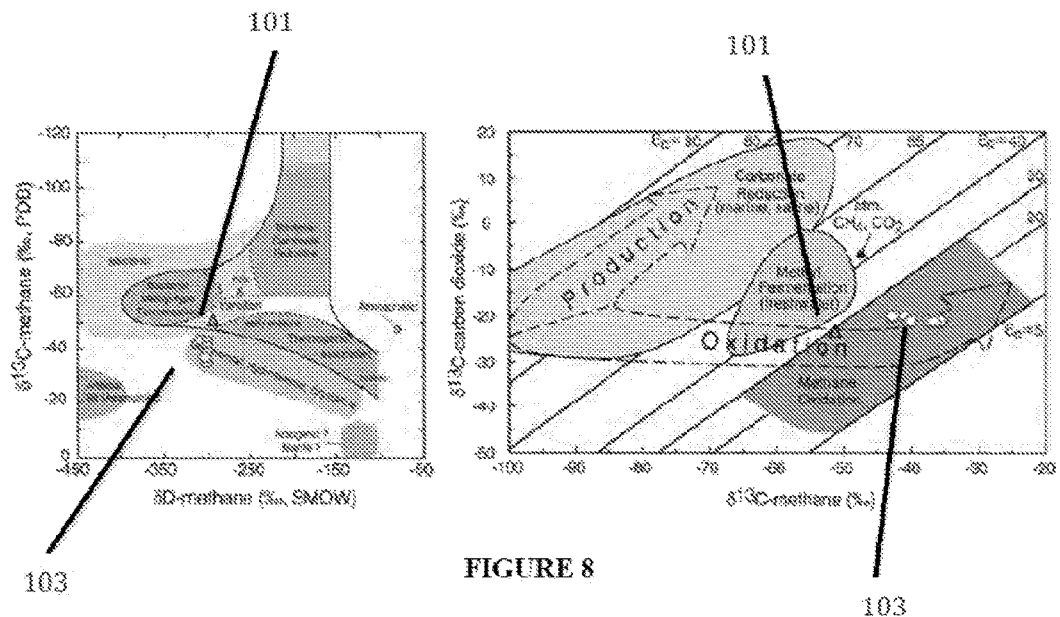
FIG. 8 shows an assessment of isotopic data from the Cranfield oil field using the system of Whiticar (1999). Blue triangle=station 101; red circles=anomaly well 103. The data indicate that $CH_4$ from well 103 originates from a deep exogenous source (i.e. the oil and gas reservoir) and $CO_2$ originates from methane oxidation. As expected, these relationships are less apparent at station 101, farther from the anomaly. The exogenous source of gas and the process of methane oxidation are successfully identified using the process-based method of analysis.

Industrial Site Cranfield Results. The base concept that background processes can be distinguished from a leakage signal using soil gas geochemical relationships was tested at the Cranfield oil field. Here, a persistent $CO_2$ (44.7%) and $CH_4$ (33.5%) anomaly is centered along a 55 m soil gas sampling transect near a plugged and abandoned well (FIGS. 5 and 7). $CO_2$ and $CH_4$ concentrations decrease and $O_2$ generally increases away from the anomaly along the 43 m that separate the anomaly and background locations. Gas sampled from the anomaly shows isotopic relationships for $CH_4$ ($\delta^{13}C$ −36.7 to −42.4‰: $\delta D$ −305.0 to −310.2‰) and $CO_2$ ($\delta^{13}C$, −18.6 to −19.8‰) that are consistent with a deep thermogenic $CH_4$ source and $CO_2$ derived from $CH_4$ oxidation (Whiticar, 1999: FIG. 8). These data confirm that the vadose-zone anomaly is exogenous gas originating from depth and provides an unambiguous setting in which to test the potential of the process-based method to perform in less obvious leakage detection scenarios. FIG. 8 shows an assessment of isotopic data from the Cranfield oil field using the system of Whiticar (1999). Blue triangle=station 101; red circles=anomaly well 103. The data indicate that $CH_4$ from well 103 originates from a deep exogenous source (i.e. the oil and gas reservoir) and $CO_2$ originates from methane oxidation. As expected, these relationships are less apparent at station 101, farther from the anomaly. The exogenous source of gas and the process of methane oxidation are successfully identified using the process-based method of analysis.

Figure 4:
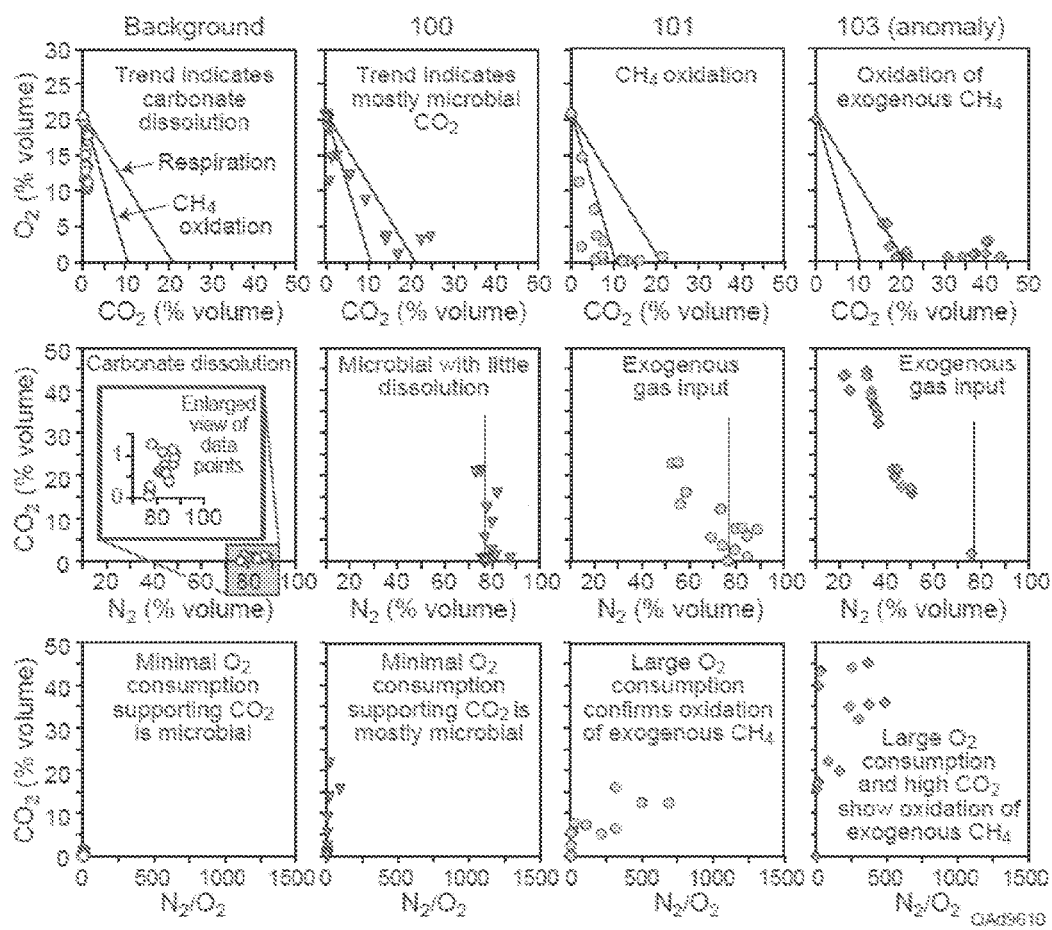
FIG. 4 shows twelve graphs that summarize the vadose zone gas data from selected wells along a gas sampling transect extending from a background location to a vadose zone gas anomaly at the P-site at the Cranfield oil field. Systematic trends (previously discussed and identified in FIGS. 1-3, at sites 100, 101 and 103 of FIG. 5) indicate that gas concentration relationships can distinguish natural background processes from exogenous gas input.

To further confirm the methodology, key gas concentration relationships ($CO_2$ vs. $O_2$, $CO_2$ vs. $N_2$, and $CO_2$ vs. $N_2/O_2$) developed at the playa site were systematically observed from the background well toward the anomaly (FIG. 4). In the background well, gas compositions fall well below the respiration and $CH_4$ oxidation trends on a graph of $O_2$ versus $CO_2$ indicating the background process of $CO_2$ dissolution and reaction with soil carbonate. In situ processes are further supported by $N_2$ concentrations enriched with respect to the atmosphere. $O_2/N_2$ is near atmospheric ratios indicating no $CH_4$ oxidation.

As the anomaly is approached along the transect, soil gas relationships between $CO_2$ and $O_2$ shift systematically toward the $CH_4$ oxidation trend line, then to low $O_2$ concentrations along that line, and finally to the right of the biologic respiration trend in the leakage field (FIG. 4). This progressive transformation represents an increasing magnitude of $CH_4$ oxidation as the anomaly is approached which eventually manifests as an exogenous source plotting in the leakage field. $N_2$ versus $CO_2$ also shifts as the anomaly is approached from a background $CO_2$ dissolution signal to one that signifies input of exogenous gas ($N_2$ concentrations<atmospheric values). $N_2/O_2$ ratios much greater than air correctly indicate persistent $CH_4$ oxidation and influx of air.

The present invention provides for the first time a new approach to separate leakage signal in the vadose zone above GCS sites from relatively complex natural $CO_2$ cycling processes without the need for background data. The approach uses three major soil gas concentration relationships ($CO_2$ vs. $O_2$, $CO_2$ vs. $N_2$, and $CO_2$ vs. $N_2/O_2$) to identify the vadose zone processes of biologic respiration, $CH_4$ oxidation, soil carbonate and $CO_2$ dissolution, atmospheric mixing, and input of exogenous gas ($CO_2$ and/or $CH_4$). Natural background processes were identified at a $CO_2$-rich playa lake in west Texas and using these techniques that were then successfully applied at an industrial oil field site near Cranfield, Miss., where exogenous gas input from depth reached the surface. At the Cranfield site, gas concentration relationships indicating natural processes shifted systematically to those indicating an exogenous gas source as a surface gas anomaly was approached. Success of the process-based approach to identify deep gas in the vadose zone at an industrial site represents a significant advance in our ability to detect $CO_2$ leakage from depth into the vadose zone at $CO_2$ storage sites.

EXAMPLE 2

Detection of Injectate Leakage from an Injected Reservoir

As shown in the insert of FIG. 1, the $O_2$ vs. $CO_2$ ratio gives an indication of the main natural processes affecting $CO_2$ concentrations. It provides a preliminary distinction among respiration and $CH_4$ oxidation (black lines and middle portion between the two lines, labelled mixture) or dissolution (bottom left area between the axis and the first line, labelled $CO_2$ dissolution). It also gives an initial assessment of leakage (top right quadrant).

Figure 9:
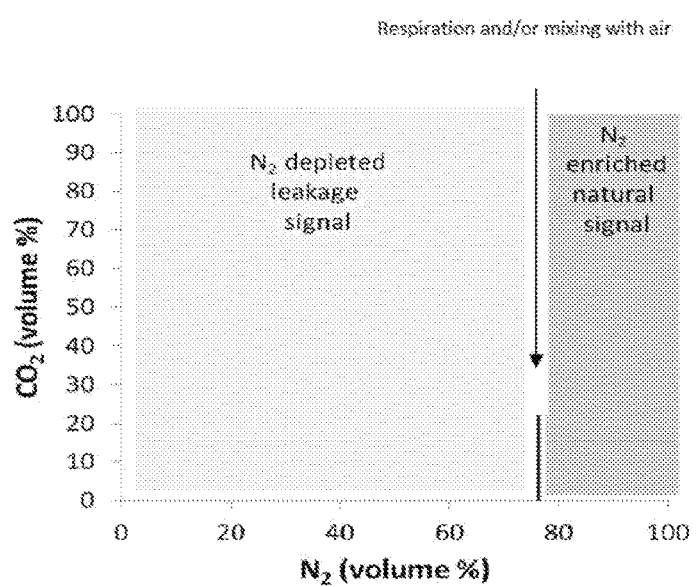
FIG. 9 shows that the $N_2$ below 76.3% (which is the $N_2$ concentration in water vapor-saturated air) indicates that exogenous gas has been added to the system (i.e., a leak of gas from depth).
Figure 10:
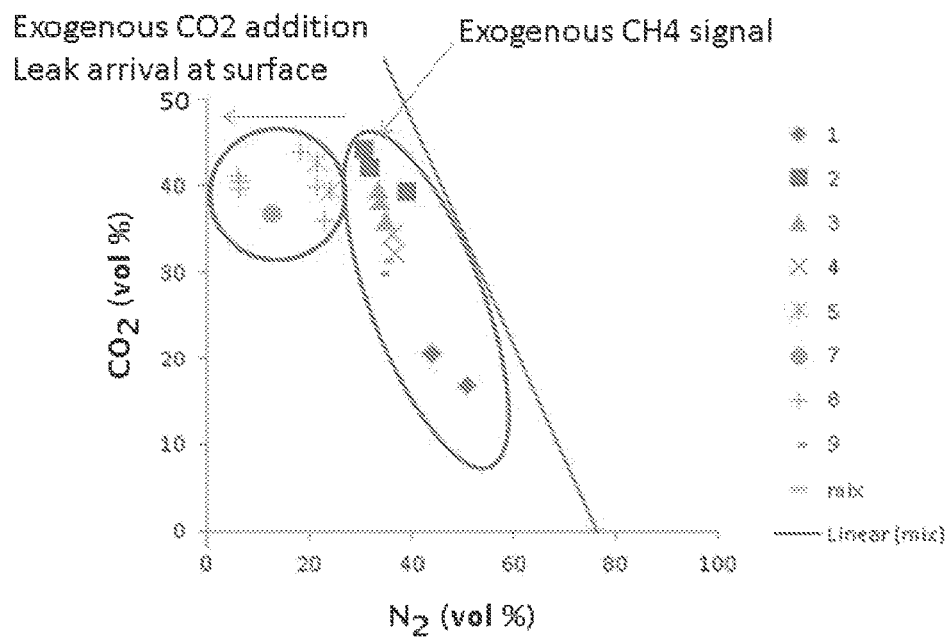
FIG. 10 shows the ratio of $CO_2$ vs. $N_2$. This is an important relationship that identifies whether gas has migrated from depth. It further indicates whether injected $CO_2$ is being added through leakage. The leakage signal of injectate $CO_2$ (data in the red circle) is apparent even in the presence of exogenous $CH_4$ migrating from depth and oxidizing to $CO_2$ (data in the blue oval).
Figure 11:
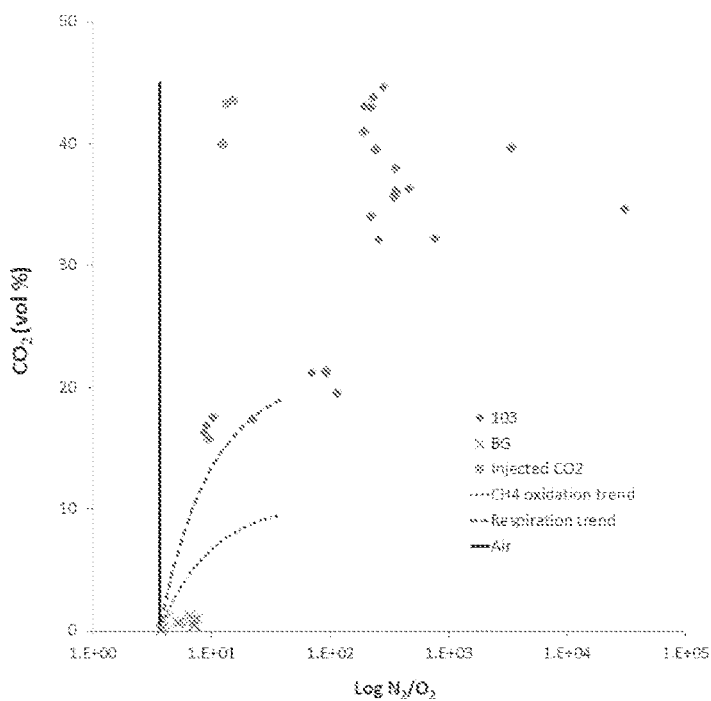
FIG. 11 is a graph that shows $CO_2$ vs. $N_2/O_2$, in which this relationship shows the degree of $O_2$ influx and consumption. Signal from injectate $CO_2$ (orange circles) is clearly distinguishable from $CO_2$ produced by oxidation of exogenous $CH_4$ to $CO_2$.

1. Measure $CO_2$ $O_2$ $CH_4$ $N_2$ (and $H_2O$ vapor if possible).
2. On a gas chromatograph, the O2 reading actually includes Ar. So is actually O2 and Ar. These gases are not separated.
3. Calculate Argon (Ar) as equal to $1/63 \times N_2$ concentration.
4. Subtract Ar from $O_2$.
5. Add water vapor content or assume saturated at 2.3%.
6. Normalize to 1 atm total pressure or 100%.
7. Observe relationships between $O_2$ versus $CO_2$ with respect to the processes of respiration and methane oxidation to get an initial idea of processes—natural or leakage (see insert, FIG. 1).
8. Observe relationships between $CO_2$ versus $N_2$ to understand if gases are being added from deep input or being lost through dissolution into groundwater (FIG. 9). Even in a complex environment where CH4 migrates from depth to the surface and becomes oxidized to $CO_2$, a leakage signal from injected $CO_2$ can be detected. $CO_2$ migrating from depth is distinguished from $CO_2$ being produced by the oxidation of $CH_4$ migrating from depth (FIG. 10). $CO_2$ leakage from depth shows an offset towards lower $N_2$ concentrations.
9. Observe relationships between $CO_2$ versus $N_2/O_2$ to understand the amount of oxygen being used in the system (FIG. 11). In a complex setting where exogenous $CH_4$ migrates from depth and oxidizes to $CO_2$, leakage of injectate $CO_2$ on top of this complex background noise can be discriminated in FIG. 11.

In operation, the relationship between $CO_2$ versus $N_2$ is evaluated to determine the processes suggested in step 6. As shown in FIG. 9, $N_2$ below 76.3% (which is the $N_2$ concentration in water vapor-saturated air) indicates that exogenous gas has been added to the system (i.e., a leak of gas from depth). $N_2$ above 76.3% indicates the background process of $CO_2$ dissolution and indicates a $CO_2$ sink (FIGS. 9 and 10).

FIG. 10 shows the ratio of $CO_2$ vs. $N_2$—This is an important relationship that identifies whether gas has migrated from depth. It further indicates whether $CO_2$ is being added through leakage (yellow field, left side of atmosphere line) or lost through dissolution (blue field, right side of atmosphere line).

Even in a complex environment where $CH_4$ migrates from depth to the surface and becomes oxidized to $CO_2$, a leakage signal from injected $CO_2$ can be detected. $CO_2$ migrating from depth is distinguished from $CO_2$ being produced by the oxidation of $CH_4$ migrating from depth (FIG. 10). $CO_2$ leakage from depth shows an offset towards lower $N_2$ concentrations.

FIG. 11 is a graph that shows $CO_2$ vs. $N_2/O_2$, in which this relationship shows the amount of $O_2$ consumed via respiration or $CH_4$ oxidation. The graph also indicates degree of air influx. In a complex setting where exogenous $CH_4$ migrates from depth and oxidizes to $CO_2$, leakage of injectate $CO_2$ on top of this complex background noise can be discriminated (FIG. 11).

Figure 12:
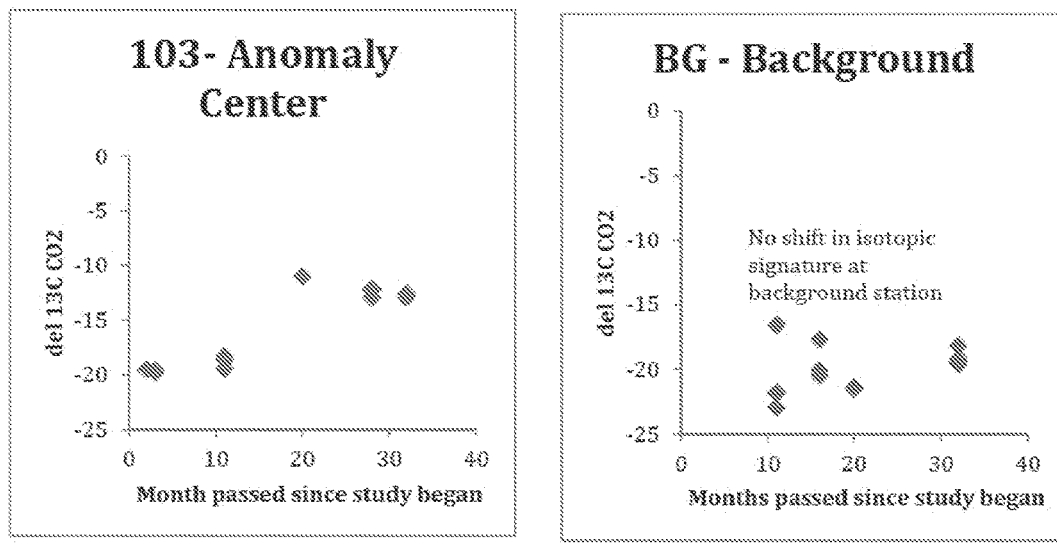
FIG. 12 includes graphs in which isotopes show a component of injectate $CO_2$ at the surface at well 103 after 20 months of monitoring, but no injectate $CO_2$ at the surface at the background well. The graphs show all isotope data taken from all 3 depths at well 103 (center of the anomaly) and all 4 depths at the background (BG) well.

FIG. 12 includes graphs in which isotopes show injectate $CO_2$ at the surface. The graphs show all isotope data taken from all 3 depths at well 103 (center of the anomaly) and all 4 depths at the background (BG) well. A shift in isotopes toward injectate values is seen at the anomaly over a 10 month period. Background samples do not show this shift.

Figure 13:
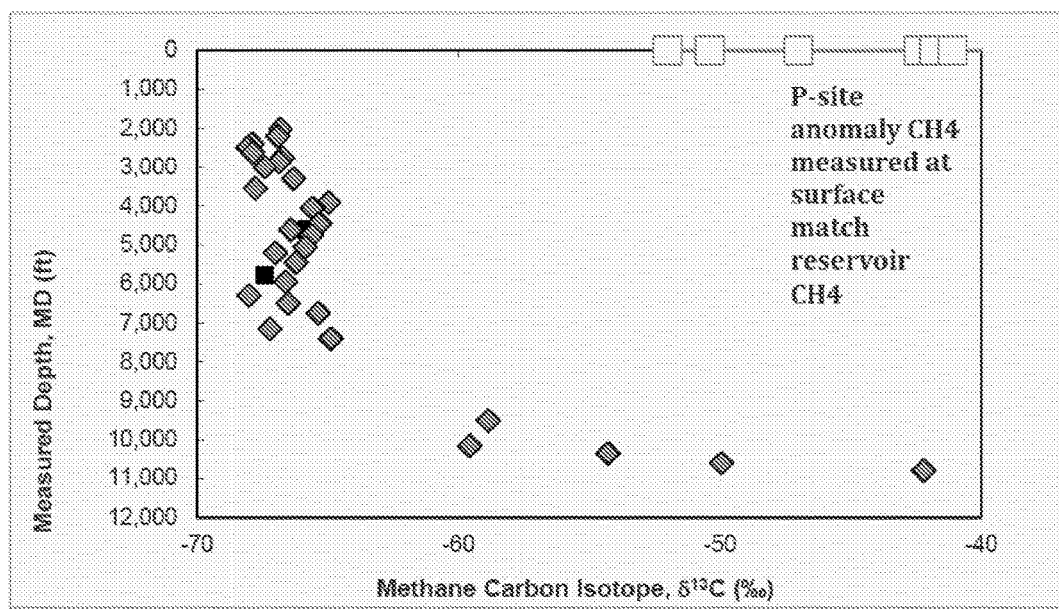
FIG. 13 shows that the P-site surface anomaly gas is isotopically similar to the producing reservoir and very dissimilar to the Wilcox and other intermediate gases suggesting the p-site anomaly originates in the reservoir where $CO_2$ EOR occurs.

FIG. 13 shows that the P-site surface anomaly gas is isotopically similar to the producing reservoir and very dissimilar to the Wilcox and other intermediate gases suggesting the p-site anomaly originates in the reservoir where $CO_2$ EOR occurs.

EXAMPLE 3

Process-based Soil Gas Leakage Assessment at the Kerr Farm: Comparison of Results to Leakage Proxies at ZERT and Mt. Etna Claims of $CO_2$ leakage at the Kerr farm near the IEAGHG Weyburn-Midale CO2 Monitoring and Storage project in Saskatchewan, Canada in 2011 presented an opportunity to test research in near-surface leakage detection at an operational setting. The claim was based on a study conducted by a private consultant that drew criticism from geologic $CO_2$ storage experts. To assess the origin of the claimed leakage, a soil gas assessment was conducted at the site using a relatively new process-based soil gas approach (Romanak et al., 2012). In order to assess leakage without years of background data or complex statistical analyses, as taught herein, this approach uses three fixed soil gas ratios (augmented by isotopic and hydrocarbon data when needed). Using this approach at the Kerr site, the relative contributions of various processes creating soil gas geochemical signatures were determined including: 1) biologic respiration, 2) $CH_4$ oxidation, 3) $CO_2$ dissolution/reaction with carbonate, 4) mixing with atmosphere, 5) degradation of historic hydrocarbon spills, and 6) $CO_2$ leakage from the storage reservoir. For additional verification, the results of the Kerr assessment were compared to new data collected at the ZERT controlled release site in Bozeman, Mont. and published data from a leakage proxy at the Mt. Etna volcano, Italy. The results from the Kerr site show no evidence for $CO_2$ leakage from the storage reservoir and also verify that a process-based approach can be used to quickly and economically assess leakage above geologic carbon storage sites. In addition, data from the ZERT release shows quantification of a leakage signal apart from natural processes is more easily accomplished using a process-based approach.

Near-surface leakage assessment at geologic carbon storage sites is important for ensuring environmental safety, responding to public concerns, and accurately determining and/or quantifying potential release to atmosphere under carbon accounting. Discriminating between natural variation and a leakage signal in the near-surface is a complex task and requires great care due to the many dynamic processes that can produce, consume, or otherwise alter soil gas in the vadose zone (e.g. Yang et al., 2013a,b). The complexity of near-surface leakage assessment increases significantly in $CO_2$-enhanced oil recovery settings where the presence of hydrocarbon gases and industrial activities add geochemical complexity (e.g. Wolayer et al., 2013). In the near surface, $CO_2$ and $CH_4$ may originate from biologic respiration, degradation of spills from historic industrial activity, or from gases migrating from depth. Gases migrating from depth may emanate from the $CO_2$ storage reservoir or other geologic zones by seepage over geologic time, historic well failures, or reservoir engineering activities. Hydrocarbons that migrate from depth to surface may readily oxidize to $CO_2$ in the vadose zone, mimicking a storage formation leak. Soil gas assessments in areas lacking background data are especially vulnerable to misinterpretation and, if not properly assessed, could lead to mistaking a natural $CO_2$ occurrence for a leakage signal.

Figure 14:
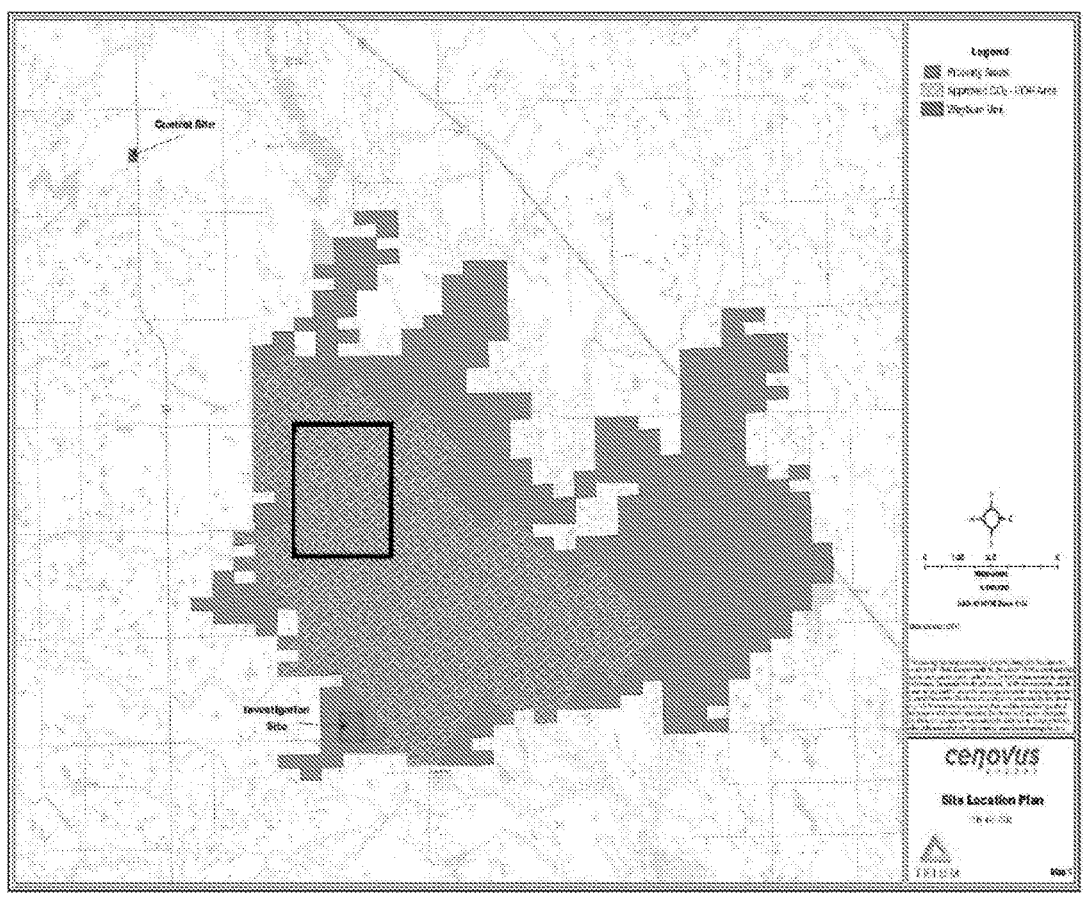
FIG. 14 is a Map showing the relative locations of the Weyburn-Midale oilfield, the Kerr Farm, and the soil gas study areas of the IEAGHG Weyburn-Midale $CO_2$ Monitoring and Storage Project (WMP). Hatched area denotes the approved $CO_2$-EOR area as of 2011. Figure is modified from Trium, 2011 showing the site for testing of the present invention.
Figure 15:
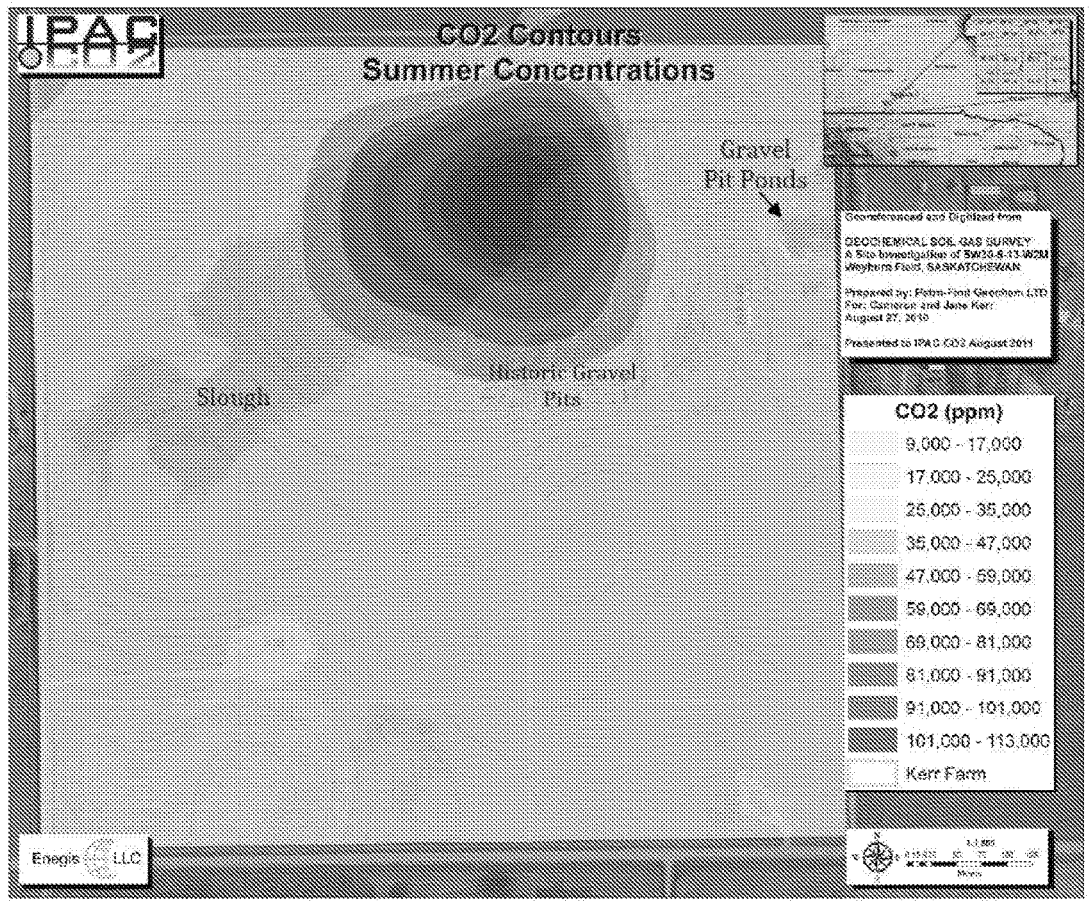
FIG. 15 is a georeferenced and digitized reproduction of the soil gas survey reported by Petro-Find Geochem Ltd. in the summer of 2010. The soil gas anomaly originally reported by Petro-Find to be the result of leakge from the Weyburn-Midale $CO_2$ Monitoring and Storage Project is shown in the nothern portion of the Kerrs propoerty and is contoured for $CO_2$ gas concentration.

The need for accurate leakage assessment was demonstrated in January 2011, when landowners living near the International Energy Agency Greenhouse Gas (IEAGHG) Weyburn-Midale $CO_2$ Monitoring and Storage Project in Saskatchewan Canada (FIG. 14) announced to the press that leaking $CO_2$ from the storage reservoir was reaching ground surface and impacting their farmland. Reported impacts were generally located in and around excavated gravel pit ponds in the NE portion of the Kerr family's quarter section. The Kerrs reported what they perceived as unusual bubbling, foaming, algal growths, and an "oily sheen" on the pond surface and dead animals in and around the ponds. In the summer of 2010, the Kerrs commissioned Petro-Find Geochem Ltd to conduct a soil gas study on the property (LaFleur, 2010), with another survey conducted in the winter of 2011 (LaFleur, 2011). Soil gas $CO_2$ concentrations measured on the property in the summer averaged approximately 2.3% with a soil gas anomaly of about 11% measured in the north portion of the property (FIG. 15). Petro-Find attributed the origin of the soil gas anomaly to injectate $CO_2$ based mostly on stable carbon isotope ratios ($\delta^{13}C$) for soil gas $CO_2$ that matched those of the $CO_2$ gas being injected into the deep reservoir, concluding: "the source of the high concentrations of $CO_2$ in soils of the Kerr property is clearly the anthropogenic $CO_2$ injected into the Weyburn reservoir" (LaFleur, 2010, 2011).

News of the supposed leaking carbon storage project flooded the media; however, experts in geologic $CO_2$ storage strongly questioned the scientific merit of the Petro-Find study (e.g. Petroleum Technology Research Centre, 2011). To address the mounting uncertainty over whether $CO_2$ leakage was actually occurring, three expert studies were independently undertaken by; 1) European scientists who conducted near-surface monitoring at the nearby IEAGHG Weyburn-Midale $CO_2$ Monitoring and Storage project (Beaubien, 2013), 2) experts commissioned by Cenovus, the oilfield operator (Trium, 2011), and 3) academic researchers commissioned by the International Performance Assessment Centre for Geologic Storage of Carbon Dioxide (IPAC-CO2) whose mission was to advance best practices and performance verification for geologic carbon storage. This Example describes the IPAC-CO2 study and how the use of a process-based soil gas approach quickly and economically determined that leakage was not occurring at the site.

An objective of the IPAC-CO2 field study was to reduce demonstrate the origin of $CO_2$ measured on the Kerr property. The study was a focused response to the soil gas surveys conducted by Petro-Find and was intended to be a targeted and timely response to landowner concerns with a conservative yet rigorous approach. The aim of the study was to assess the degree to which the gases present in the soil on the Kerr property were: 1) the result of natural (biological or geological) variability, 2) the result of leaks or spills associated with oil producing activities on the site, and/or 3) associated with $CO_2$ leakage from the $CO_2$-enhanced oil recovery in the underlying Weyburn-Midale reservoir. Study objectives concentrated on two broad focus areas which represents further proof of a process-based approach to near-surface leakage assessment: (1) Determine whether gases originating in the deep subsurface have migrated to the near-surface: Evidence of deep gases in the near-surface indicates a potential avenue of gas transport from the reservoir but is not proof in itself that injectate $CO_2$ has migrated to the surface. Seepage from several intermediate hydrocarbon-bearing reservoirs and/or seepage of deep accumulations of $CO_2$ that exist in the subsurface beneath the study area were plausible. (2) Identify major in-situ processes active in the vadose-zone: Knowledge of carbon cycling processes is critical to correctly assessing the origin of soil gases and understanding the potential transformations that may have occurred since their formation.

A process-based analysis of fixed soil gases ($CO_2$, $N_2$, $O_2$, $CH_4$) was used to meet the study objectives. If needed, interpretations made using a process-based analysis of fixed soil gases can be augmented with isotope ratios and hydrocarbon concentration data. To ensure the accuracy of observations and conclusions of the near-surface investigation, soil gas geochemical relationships observed at the Kerr Farm were compared to those observed at two leakage proxy sites; 1) the Zero Emission Research and Technology Center (ZERT) site where soil gas measurements were made under a controlled leakage scenario: and, 2) Mt. Etna volcano where volcanic gases migrate from depth to the surface. Comparing the geochemical ratios observed at the Kerr site with ratios from $CO_2$ leakage proxy sites is important for verifying the presence or absence of an actual leakage signal at the Kerr Farm.

Leakage Proxy Comparison. The process-based method of soil gas analysis was first developed at a $CO_2$-rich perched wetland (a feature known as a "playa lake") in West Texas, USA. Here, a high level of in-situ biologic gas production, dissolution of $CO_2$ into recharging groundwater and $CH_4$ oxidation could be systematically observed and coupled with characteristic geochemical ratios for each natural process (Romanak, 1987; Romanak et. al., 2012). No $CO_2$ leakage input from depth was present at the playa lake; therefore, soil gas ratios that would represent leakage could only be conceptualized. Additional verification of these concepts was achieved at a Gulf Coast oilfield where a process-based method successfully identified exogenous (i.e., originating from the reservoir) $CH_4$ in shallow sediments near a 1950s plugged and abandoned well (Romanak et. al., 2012). Pre-injection at the oilfield, isotopic analysis of gases indicated that $CH_4$ measured in the vadose zone originated within an oil and gas reservoir at depth, and that shallow $CO_2$ was produced from $CH_4$ oxidation. This proxy gives an idea of how process-based geochemical ratios can be used to identify exogenous methane input from depth and the secondary $CO_2$ signal created by methane oxidation, but is not a straightforward example of a primary $CO_2$ leakage signal. Therefore, to gain more experience with the simple case of $CO_2$ leakage input, the process-based analysis at the Kerr farm is compared with: 1) the ZERT field site (Spangler et al., 2010) where leakage of $CO_2$ into the near-surface is simulated; and, 2) a process-based analysis of data published in the literature and collected at Mt. Etna volcano where magmatic $CO_2$ migrates from depth to surface (Giammanco et al., 1998). Through an integration of these case studies, the process-based method not only is used to assess leakage at the Kerr site but also is proven as a tool for quick and economical response to landowner claims of leakage near geologic carbon storage sites.

Figure 16:
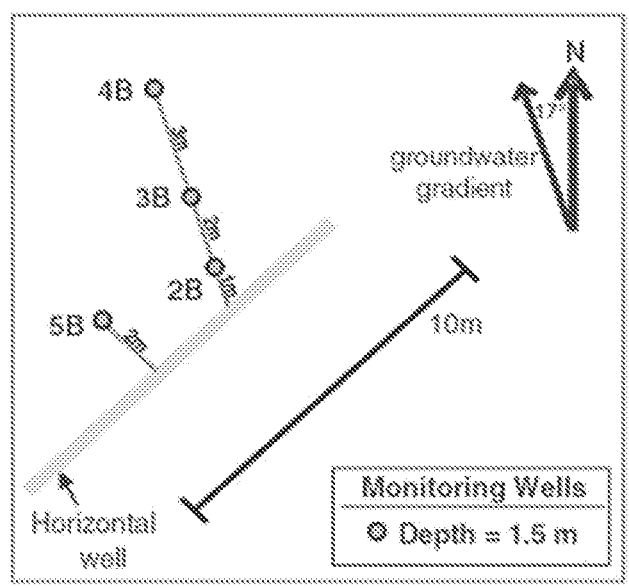
FIG. 16 is a ZERT site map showing wells used for vadose zone sampling (2B, 4B, 5B). Well 3B was used for groundwater monitoring (Romanak et al., 2013). Location of the horizontal well used for controlled $CO_2$ release is shown. Map modified from Kharaka et al. (2010).

ZERT Site. In addition, the results from the Kerr Farm are compared to new research results from a controlled release study at the ZERT site where a leakage signal was artificially induced in the near-surface and monitored using a process-based approach (Romanak et al., 2013). The ZERT location provides a simple environment in which to observe the geochemical signature of $CO_2$ leakage input without the complexity of co-existing hydrocarbons. The field site is located in the Gallatin Valley about 700 km SW of the Kerr Farm on agricultural land owned by Montana State University in Bozeman, Mont. (Spangler et al., 2010). Locally at the test site, as much as 1.2 m of organic-rich silt and clay is underlain by silicic sandy gravel with a caliche layer at 0.5 to 0.8 m depth (Kharaka et al., 2010; Spangler, 2010). To simulate leakage, $CO_2$ at the site is released from a 100-m-long, 10-cm-diameter slotted pipe installed at ~1.8 m depth within a silicic sand-gravel aquifer with a trace of carbonates (Kharaka et al., 2010). The fixed gas relationships monitored at three locations during the $CO_2$ release provide a controlled proxy for $CO_2$ leakage into the near-surface (FIG. 16).

Mt. Etna Volcano. Despite differences in some conditions such as biologic activity and $CO_2$ flux rates, volcanic regions can serve as a general proxy for $CO_2$ leakage and can illustrate the general geochemical relationships expected if $CO_2$ were to invade the near surface from depth. The concept of using volcanic gas emissions as a proxy for a storage formation leak has been used by others (e.g. Jones et al., 2003; Beaubien et al., 2004; Riding and Rochelle, 2005). The present inventors sow herein a process-based analysis of published soil gas data from Mt. Etna as a comparative example (Giammanco et al., 1998). Mt. Etna, one of the most active stratovolcanoes in the world is located in eastern Sicily, Italy. Here, all gases of interest for a process-based analysis were measured from crater fumaroles that appear to be related to fractures and from soils on the volcano's flanks (Giammanco et al., 1998).

Regional and Local Geologic Setting at the Kerr Site. The Weyburn-Midale field, located in southeastern Saskatchewan, Canada produces from within Ordovician, Devonian and Mississippian rocks (Saskatchewan Geological Survey, 2003). The carbonate beds of the Madison Group including the Charles Formation at a depth of about 1500 m are particularly important in this area (Saskatchewan Ministry of Energy & Resources (SER), 2011). In addition to the numerous oil and gas bearing formations found beneath the Weyburn-Midale production zone, at least two Triassic-Jurassic oil-bearing units and two Upper Cretaceous-Tertiary lignite-bearing units also exist (SER, 2011). Natural accumulations of magmatic $CO_2$ are documented in Devonian and Cambrian formations in southwestern Saskatchewan (Whitaker et al., 2004) and may possibly be present beneath the Kerr property. Gases from any of these formations could potentially migrate to the surface over geologic time.

Regional Cenozoic stratigraphy of the Weyburn Valley, Saskatchewan, Canada is glacial-fluvial drift approximately 175 meters thick deposited unconformably upon the Cretaceous Pierre Shale (Simpson, 1993). Sequential cycles of glacial advance and retreat resulted in erosion and deposition of a highly heterogeneous, interbedded glacial-fluvial sedimentary section comprised of stratified and interbedded clays, silts, sands, and gravels. The complex stratigraphic heterogeneity causes disconnected sand and gravel-rich lenses. At the Kerr Farm (SW Section 30, Township 5, Range 13, W2M) near-surface sediments include approximately 60 m of interbedded glacial-fluvial clay, silt, sand, gravel, pebbles, and boulders (Simpson, 1993; Aqua Terre, 2006). Surface water is found in several gravel excavation pits at the site and in a 200-m-long, northeast-southwest trending slough located approximately 75 m to the northwest of the Kerr residence.

Process-based Leakage Detection Method. A process-based soil-gas approach is a direct, fast and economical way to assess near-surface leakage and to determine if environmental impacts arise from a storage formation leak or from natural variation, as outlined in the Examples hereinabove. This method aims to identify whether deep gas (either $CH_4$ or $CO_2$) has invaded the shallow subsurface (i.e. the vadose zone) or if gas has been produced and or altered in the shallow subsurface. Examples of vadose zone processes influencing soil gas concentrations of $CO_2$ in the shallow subsurface include: 1) near surface microbial and root respiration; 2) $CO_2$ dissolution and reaction with soil carbonate; 3) oxidation of methane that is either biologically produced or originates from depth; 4) atmospheric mixing/dilution; and, 5) leakage of $CO_2$ from the storage reservoir into the near-surface.

Figure 17A:
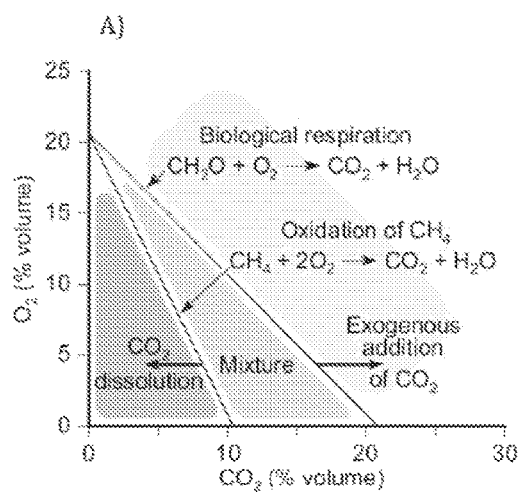
FIGS. 17A-17C show the ratios used in a process-based analysis to distinguish leakage signal from natural variation in the near-surface above geologic carbon storage sites.
Figure 17B:
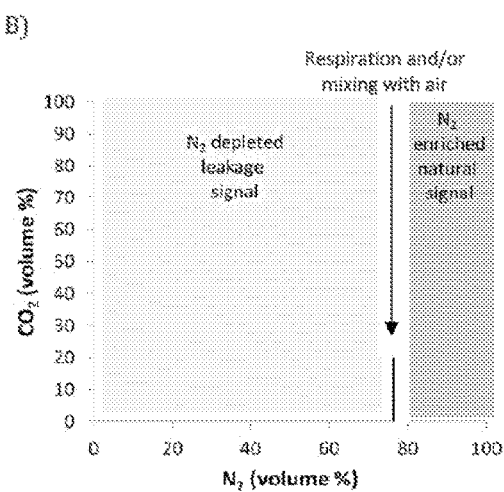
Figure 17C:
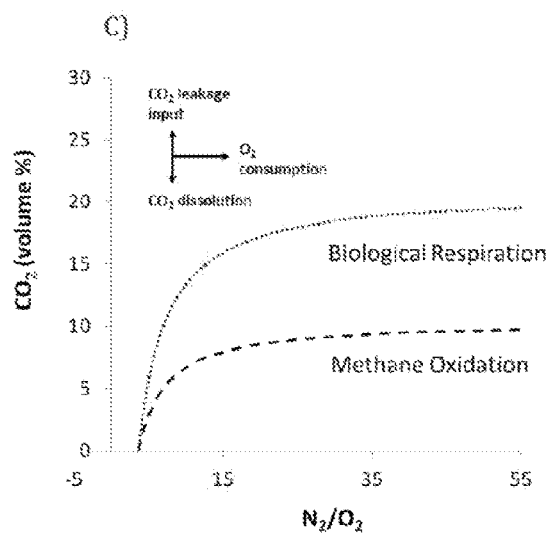

The conceptual approach is based on the use of three geochemical relationships to characterize vadose zone processes that affect the composition and isotopic signature of soil gases and to indicate whether an active pathway of gas migration from depth to the surface exists (FIGS. 17A-17C). Once these processes are understood, the dominant sources of these gases can be determined with reasonable certainty even in the absence of background data or when naturally occurring in-situ and exogenous gases are mixed.

Fixed gases. The various processes that produce and consume $CO_2$ have been shown to affect soil gas concentrations of $N_2$, $O_2$, and $CH_4$ in predictable ways (Romanak, 1997; Riding and Rochelle, 2005; Romanak et. al., 2011, 2012). The ratios of, or correlations among, these various gas component concentrations can help identify whether a signal is natural background noise or deep reservoir leakage. Analysis of detailed isotopic signatures and any existing hydrocarbon gases provides increased certainty in the interpretation of results.

Beginning with the composition of the natural atmosphere (78% $N_2$, 21% $O_2$, 0.0385% $CO_2$, 1.7-2.0 ppm $CH_4$), carbon cycling processes in the unsaturated zone will alter the geochemistry of soil gas in predictable ways that can be used to identify the processes involved. The level of certainty is increased by examination of several different relationships in sequence; $O_2$ versus $CO_2$, $CO_2$ versus $N_2$, and $CO_2$ versus $N_2/O_2$ (FIG. 1 inset). These relationships are described in more detail below.

Biologic respiration utilizes $O_2$ as the terminal electron acceptor for energy production and produces $CO_2$ as a by-product according to the reaction:

$$CH_2O + O_2 \rightarrow CO_2 + H_2O \qquad (1)$$

When the supply of organic matter outpaces that of $O_2$, anaerobic bacteria utilize alternate electron acceptors ($SO_4^{2-}$, $NO_3^-$, $Fe^{3+}$ and oxyhydroxides) when available. In the absence of these electron acceptors, $CH_4$ is produced. When $CH_4$ migrates into oxic zones, or environmental change results in an influx of $O_2$ into a previously anoxic, $CH_4$-producing environment, $CH_4$ is oxidized to $CO_2$ according to the following equation:

$$CH_4 + 2O_2 \rightarrow CO_2 + 2H_2O \qquad (2)$$

These common biologic processes result in predictable deviations from atmospheric concentrations for $CO_2$ and $O_2$ along a trend with a slope of −1 for biologic respiration and −2 for methane oxidation (FIG. 9). Addition of $CO_2$ such as might be released from a storage formation will create $CO_2$ concentrations larger than would be expected from corresponding $O_2$ concentrations based on these relationships. Alternatively, $CO_2$ concentrations less than those predicted from $O_2$ concentrations may signal a loss of $CO_2$ due to dissolution and reaction with soil carbonate (Romanak, 1997; Romanak et. al, 2012).

Further knowledge of the carbon cycling processes that have occurred, and further certainty in the correct interpretation of measurement results can be gained by studying the relationship of $N_2$ with $CO_2$. Because gas concentrations are measured in percent (by volume or molar), any non-reactive addition or subtraction of a gas component will, by definition, dilute or concentrate (respectively) all other gas components in a gas mixture. $N_2$, a relatively non-reactive but major component in air and soil gas can be used to indicate this process. Used in conjunction with the relationships between $CO_2$ and $O_2$ described above, $CO_2$ that shows a negative correlation with $N_2$ signals dilution by input of exogenous gas (Riding and Rochelle, 2005) and $CO_2$ that shows a positive correlation with $N_2$ indicates dissolution of $CO_2$ and reaction with soil carbonate (Romanak et. al, 2012). In the case of $CO_2$ dissolution and reaction with soil carbonate, the resulting loss of pore pressure from loss of a gas component into the aqueous phase may create advection of air (78% $N_2$) into the pore, enhancing enrichment of $N_2$ above atmospheric concentrations (Romanak, 1997).

Because $N_2$ essentially acts as a conservative tracer within the gas mixture, the ratio of $N_2/O_2$ can be used as a measure of the degree to which $O_2$ is consumed in the system (FIGS. 17A-17C). Ratios above atmospheric (3.7) illustrate that $O_2$ is being consumed. According to equations 1 and 2, $O_2$ consumption results from respiration and even more so during $CH_4$ oxidation; therefore in environments where $CH_4$ is present, a high $N_2/O_2$ value can signal the degree to which $CH_4$ oxidation is occurring. When $CH_4$ is constantly fluxing from depth into the near-surface, these ratios can become several orders of magnitude larger than atmospheric ratios.

Isotopic Data. Isotopic data provide important information about the origin of $CO_2$ and $CH_4$ in soil gas and the processes that gave rise to their formation (Schoell, 1983, 1988; Faber et. al., 1992; Rice, 1993; Whiticar, 1994, 1999). Coupled with analysis of fixed gas ratios and compared to data on higher hydrocarbons ($C_2$-$C_6$), analysis of isotopic signatures can provide a high level of certainty in the identification of the origin of $CO_2$ and $CH_4$ in soil gas. Carbon isotopes of $CO_2$ and $CH_4$ can be compared to distinguish between $CO_2$ that forms from biologic fermentation and that which forms from oxidation of $CH_4$. This information is especially important in organic-rich wet environments such as the prairie pothole wetlands of Saskatchewan where environmental factors support a wealth of biologic activity. If fixed gas and isotopic data indicate biologic origin of the $CO_2$, the likelihood that environmental anomalies are due to $CO_2$ injection practices is diminished. If methane oxidation is indicated as a major source of $CO_2$, the source of methane must be determined as it may be from deep gas migrating from a storage formation or from a shallow biologic source. In either case, it is important to separate primary formation of $CO_2$ from secondary formation of $CO_2$ that results from methane oxidation.

The stable isotopes of methane ($\delta^{13}C$ and $\delta D$) can provide information for determining whether methane is biogenic (shallow-sourced) or thermogenic (deep sourced) (Schoell, 1983, 1988; Faber et. al., 1992; Rice, 1993; Whiticar, 1994, 1999). The presence of methane may indicate one or more significant facts regarding the source of $CO_2$: 1) at least some, if not all $CO_2$ may be of a secondary origin in that it originates from methane oxidation; and, 2) the presence of thermogenic methane in the near-surface indicates a pathway of migration from depth. Migration may be from the storage reservoir or from intermediate reservoirs and does not necessarily indicate that $CO_2$ has migrated out of the storage formation. This second outcome presents a scenario where more work would be needed to fingerprint the actual formation from which gas has migrated.

The relationship of $\delta^{13}C$ of $CH_4$ with $C_1/(C_2+C_3)$ according to Whiticar (1999) provides additional information that improves the certainty that measured gases are either biologic or thermogenic and also provides information on the potential effects of transport and mixing. The information gained here may indicate from which type of reservoir deep gas migrates; kerogen type II (oil and gas) or kerogen type III (coal), and can, indicate whether gas is likely leaking from the storage reservoir or seeping naturally from an intermediate formation.

Hydrocarbons. Significant difficulty can be encountered when working in an area of petroleum production where a variety of sources of anthropogenic hydrocarbon gases can be confused with natural seeps and/or shallow biologic activity. Anthropogenic sources may include gasoline contamination or fresh or weathered crude oil spills and must be distinguished from natural seeps (Marrin, 1988, 1991; Ostendorff and Hampbell, 1991; Ririe and Sweeney, 1993). For example, soil gas resulting from gasoline spills is high in $C_5$ and $C_6$ components relative to lighter hydrocarbons. Crude oil spills tend to be relatively rich in $C_3$-$C_5$ components unless weathering has removed the light fractions, decreasing $C_2$, $C_3$, and $C_4$ relative to a fresh crude spill.

Hydrocarbons also may result from in-situ microbial activity. Baseline soil gas data collected in the summer and fall of 2001 as a part of the Weyburn-Midale $CO_2$ Monitoring and Storage Project included detection of $CH_4$, $C_2H_6$ and $C_3H_8$ (Riding and Rochelle, 2009). Distribution of $C_2H_6$ was similar to that of $CH_4$. Temporal variations in $C_2H_4$ and $C_3H_8$ were similar to those of $CO_2$, with concentrations decreasing significantly over successive seasons. These geochemical relationships led researchers to conclude a shallow biological origin for these hydrocarbon gases.

Seeps are best identified using $C_2+$ analyses because of the predictable effects that migration from the reservoir to the near-surface and ensuing oxidation has on hydrocarbon gas concentrations (Klusman, 2003a; 2003b; 2006; 2011). In nearly all oil fields, relative abundances of the alkanes (paraffins) are generally $C_2H_6 > C_3H_8 > C_4H_{10}$. Differences in migration and oxidation rates among $CH_4$ and light alkanes during seepage result in a reversal of these relationships, with $C_4H_{10} > C_3H_8 > C_2H_6$ in unsaturated zone soil gas (Ronald W. Klusman, personal communication; Klusman, 2011).

When combined, general hydrocarbon distributions within a gas sample, isotopes of $CH_4$ and $CO_2$, and fixed soil gas analyses may indicate whether a signature most likely results from a seep, hydrocarbon spill, or in-situ microbial activity. If hydrocarbon data remain ambiguous, comparison of isotopic signatures of each individual hydrocarbon species (e.g. Szatkowski et al, 2002; Tilley and Muehlenbachs, 2006) with those in the reservoir may be necessary for definitive sourcing.

At the Kerr Farm, soil gas sampling locations were chosen to target areas of the 2010 and 2011 Petro-Find $CO_2$ anomalies (LaFleur, 2010, 2011) (FIGS. 5, 6); however, locations available for well stations were constrained by setback requirements from oil field and utility infrastructure, agriculture activities at the site, and by the wetland habitat (slough and gravel pit ponds) of the protected Northern Spotted Leopard Frog. Boreholes for ten soil gas sampling stations were drilled at the Kerr site with sediment samples collected during auger drilling to characterize subsurface lithology. Sediment was collected from the flights of the drilling rig auger at 0.3-m intervals to maximum borehole depth and collected in clean 250 ml high-density polyethylene (HDPE) bottles labeled with the station name, date, and sample depth. A portion of the sediment sample was also used to classify color and sediment properties. Color was estimated by visual inspection using a Munsell Soil Chart (Munsell, 1975). Relative moisture content (i.e., dry, damp/moist, wet) was assigned to each depth interval to estimate groundwater level. Sediment type (i.e., sand, gravel, silt, clay) was characterized in the field using the Unified Soil Classification System (USCS) method (American Society of Testing and Materials, 2011). Sediment samples were stored on ice and subsequently placed in a freezer at the University of Regina for long-term storage.

Figure 18:
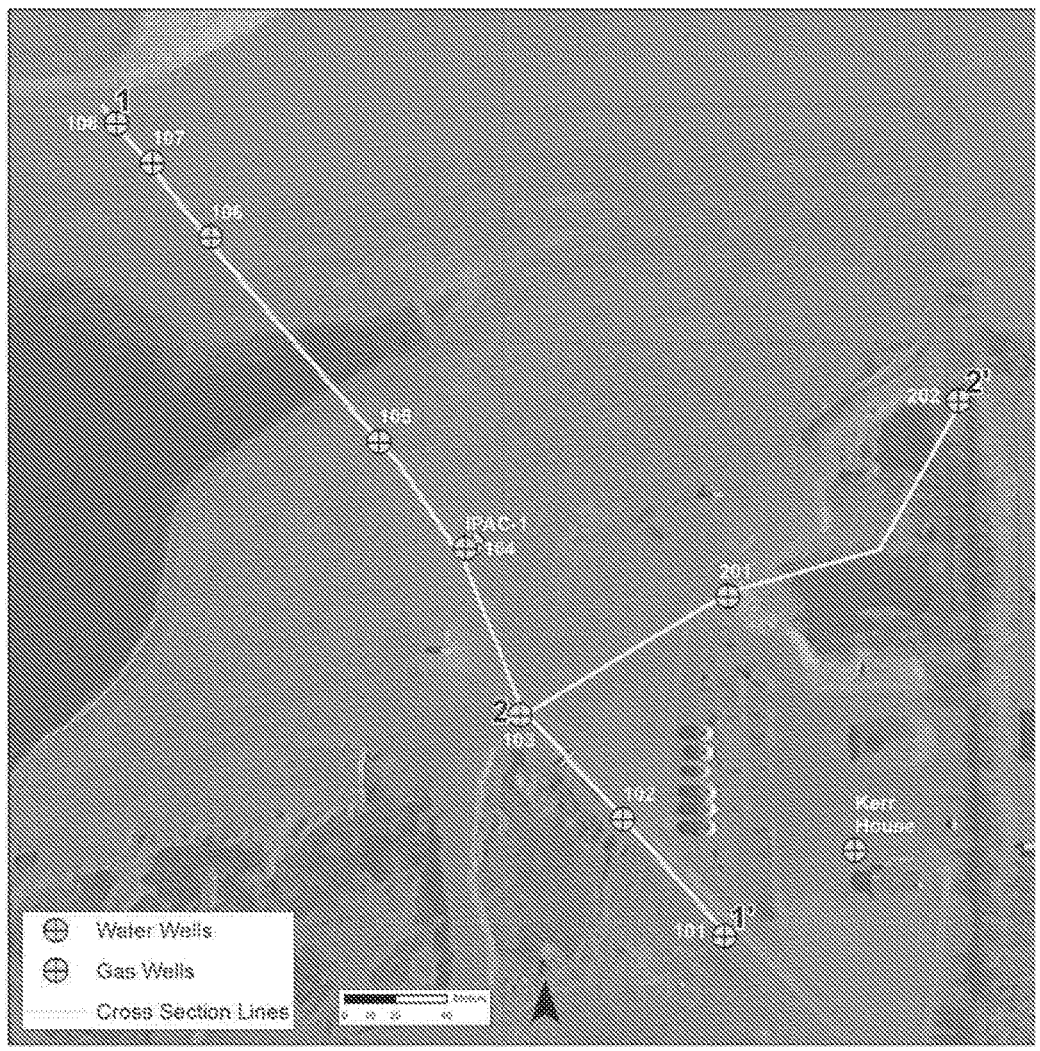
FIG. 18 is an aerial view of property owned by Cameron and Jane Kerr near Goodwater, Saskatchewan (SW Section 30, Township 5, Range 13, W2M). Locations of soil-gas sampling stations, shallow groundwater wells and cross section locations are shown. Hydrogeologic cross sections are indicted by lines 1-1' and 2-2'. Historic aerial photo does not fully represent surface hydrologic conditions at the time of the IPAC-$CO_2$ study. (Aerial photo courtesy of SER).
Figure 19:
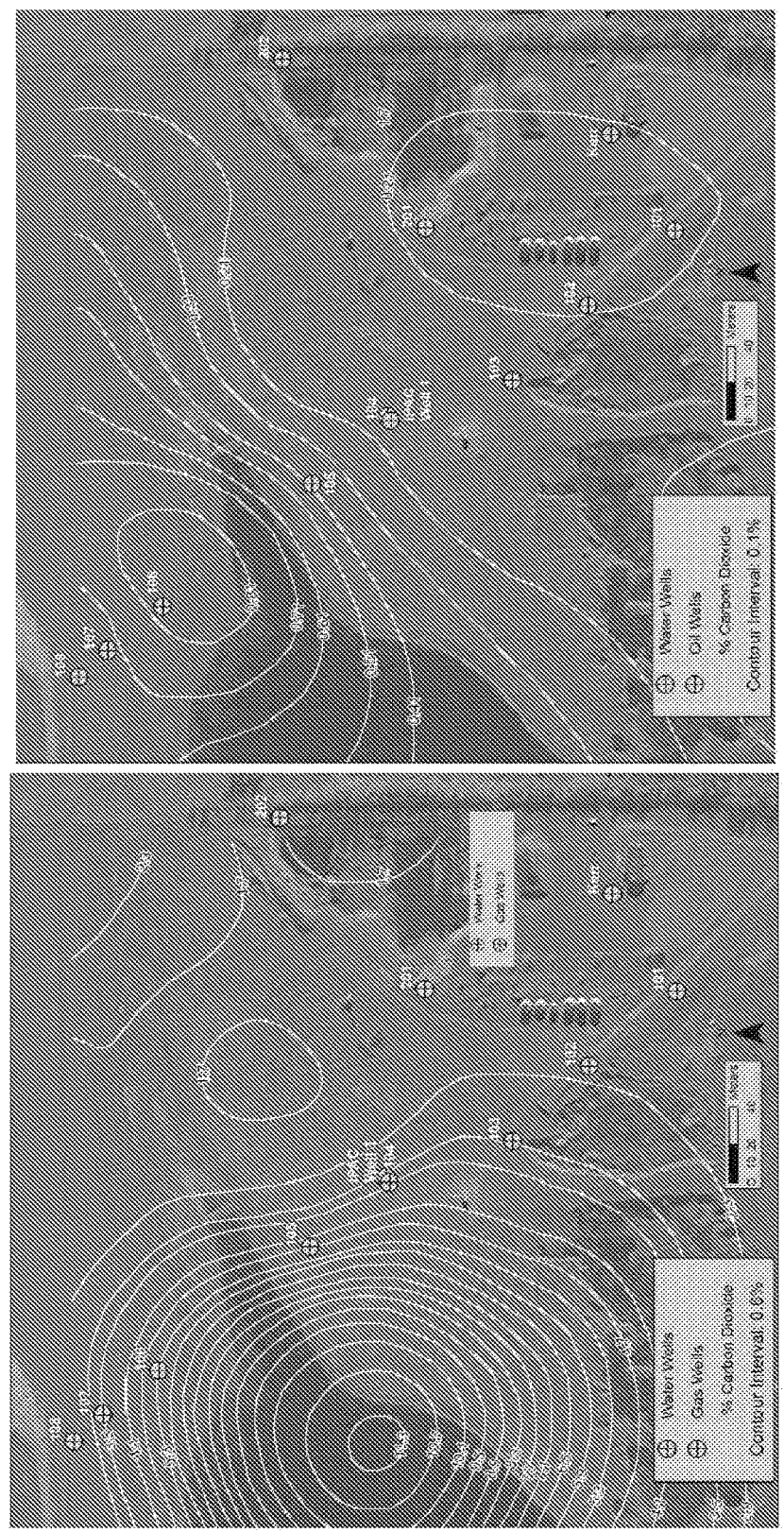
FIG. 19 shows the soil gas stations and water well locations with respect to the summer 2010 Petro-Find $CO_2$ anomaly (left) and winter 2011Petro-Find $CO_2$ anomaly (right). Historic aerial photo does not fully represent surface hydrologic conditions at the time of the IPAC-$CO_2$ study. (Aerial photo courtesy of SER).

Ten semi-permanent soil gas sampling stations, each consisting of sampling ports set at multiple depths were installed within the boreholes at the Kerr Farm. Sampling port installation and design is described in the auxiliary material in Romanak et al. (2012). One main transect (transect 1-1' comprising eight stations) extended from an area of minimal $CO_2$ as measured by Petro-Find (representing site background conditions) northwest across areas of Petro-Find $CO_2$ anomalies in the northeast portion of the quarter section. This transect also passed nearby a water injection well that disposes reservoir brine associated with oil field operations and across a slough in the north central portion of the property. FIG. 18 is an aerial view of property owned by Cameron and Jane Kerr near Goodwater, Saskatchewan. A second lesser transect (transect 2-2' comprising three stations, one common to the main transect) includes the north and west portions of the gravel pit where various phenomena were reported by the Kerrs (EcoJustice, 2010). (FIG. 19).

At the ZERT site, gas was sampled from pre-existing 5-cm-diameter PVC water monitoring wells located 1-6 m down gradient from the controlled $CO_2$ release (FIG. 16). These wells were slotted both in the saturated and unsaturated zones. A custom-made double packer system was used to isolate and sample gases over a 0.15 m interval from the vadose zone portion of slotted PVC pipe at a depth of 1 m below ground surface. At the time of sampling, depth to groundwater was 1.4 meters and $CO_2$ was released at ~1.8 m depth in a sand and gravel aquifer. Gas was sampled from wells 5B, 3B, and 4B, each located at different distances from the release well, from 9 Jul., 2012 at 09:00 to 13 Jul. at 16:00 and again from 15 Jul. at 20:12 to 18 Jul. at 20:48. On 10 Jul. at 18:00, a release of 0.15 tonne/day of $CO_2$ began at the site. The release was interrupted between 11 Jul. at 17:15 and 15 Jul. at 18:15 when equipment failed due to a lightning strike.

For both studies, soil gas concentrations of $CO_2$, $N_2$, $O_2$ and $CH_4$ were determined by gas chromatography in the field with additional gas samples collected in Cali 5-Bond® gas bags for laboratory analysis. Laboratory analyses included $CO_2$, $N_2$, $O_2$, Ar, $CH_4$, $C_2$-$C_5$ alkanes/alkenes and ($\delta^{13}C$) of $CO_2$ for the Kerr data set. All laboratory analyses were conducted by Isotech Laboratories (Champagne, Ill.) using gas chromatography coupled with an online isotope ratio mass spectrometer (GC-C-IRMS). Stated precision for $\delta^{13}C$ is +/−0.3‰. Stated precision for the gas concentrations is +/−2% of the reported value with a lower quantification limit of 3 ppm (0.0003%). Thus, an uncertainty of +/−3 ppm should be used in place of +/−2% for values less than 150 ppm. The lower limit of detection is given as 1 ppm. Data were reduced for interpretation by adding 2.2% water vapor (the saturated condition at ambient temperature and pressure) to each sample and normalizing total gas concentrations to 100% for comparison purposes.

Two stratigraphic cross sections (FIGS. 20, 21) were made using generalized sediment sample lithologic descriptions and moisture content from gas well boreholes. Land surface elevation is from Altus Geomatics (2011). Total well borehole depths ranged from 3.7 to 5.8 m below ground surface (Table 1). Generalized site geology is comprised of a thin, irregular soil veneer, which overlies several meters of sand and gravel. Silt and clay underlie the site down to maximum borehole depth. Mature soil horizons are present in boreholes of six of the ten stations and range from a total depth of 0.3 to 1.2 m. Sand and gravel were found in all but one station (107) and typically was found at the surface or just below the soil horizon down to a depth of 2.1 to 4.6 m. Silt and clay were found in eight boreholes. The top of the silt/clay layer started at 0.6 to 3.4 m depth and continued to a depth of 0.9 to 5.5 m. Although boreholes were drilled to a depth of nearly 6 m, borehole sections with sands and gravels often collapsed below the water table.

TABLE 1

Characteristics of soil gas wells.

| Station | 101 | 102 | 103 | 104 | 105 | 106 | 107 | 108 | 201 | 202 |
|---|---|---|---|---|---|---|---|---|---|---|
| BOREHOLE DEPTH | | | | | | | | | | |
| m msl | 576.6 | 578.0 | 575.7 | 576.0 | 575.8 | 575.1 | 575.9 | 577.0 | 576.3 | 575.4 |
| m bgs | 4.6 | 3.0 | 4.6 | 3.7 | 3.7 | 4.6 | 5.5 | 5.8 | 4.0 | 4.6 |
| GAS SAMPLE DEPTH | | | | | | | | | | |
| Well 1 | 580.0 | 580.2 | 579.7 | 579.1 | 578.8 | 579.1 | 579.8 | 581.3 | 579.6 | 579.3 |
| Well 2 | 579.5 | 579.6 | 579.2 | 578.8 | 578.2 | 578.6 | 578.3 | 579.8 | 579.2 | 578.7 |
| Well 3 | 578.5 | 578.9 | 578.8 | 577.7 | — | 577.6 | 576.9 | 578.3 | 578.6 | 578.3 |
| Well 4 | — | — | — | — | — | — | 575.6 | 577.2 | — | — |
| GROUNDWATER LEVEL | 579.0 | 579.2 | 578.8 | 579.0 | 578.8 | 578.8 | — | — | 579.0 | 579.0 |
| SEDIMENT DEPTHS | | | | | | | | | | |
| Soil Top | — | — | — | 579.6 | — | 579.7 | 581.4 | 582.8 | 580.2 | 579.9 |
| Soil Bottom | — | — | — | 579.0 | — | 579.1 | 580.4 | 582.2 | 579.0 | 579.6 |
| Sand/Gravel Top | 581.1 | 581.1 | 580.3 | 579.0 | 579.5 | 578.8 | — | 579.5 | 579.0 | 579.6 |
| Sand/Gravel Bottom | 577.8 | 577.7 | 576.9 | 577.5 | 576.7 | 577.0 | — | 578.9 | 577.8 | 575.4 |
| Silt/Clay Top 1 | 577.8 | — | 576.9 | 577.5 | 576.7 | 579.1 | 580.4 | 582.2 | 577.8 | — |
| Silt/Clay Bottom 1 | 576.6 | — | 575.7 | 576.0 | 575.8 | 578.8 | 575.9 | 579.5 | 576.3 | — |
| Silt/Clay Top 2 | — | — | — | — | — | 577.0 | — | 578.9 | — | — |
| Silt/Clay Bottom 2 | — | — | — | — | — | 575.1 | — | 577.0 | — | — |

All values are elevations presented in meters relative to mean sea level (msl); however, borehole depths also are shown as meters below ground surface (bgs). Not applicable is indicated by a '—' symbol.

$CO_2$ concentrations ranged from non-detectable at station 107 on the north side of the slough, to 7.5% at station 104 on the south side of the slough. The 7.5% $CO_2$ value was measured near the eastern edge of the summer 2010 Petro-Find anomaly (maximum $CO_2$ of 11%) and near a zone of high $CO_2$ concentration measured in the northeastern portion of the property by Petro-Find in the winter of 2010 (0.88%). Differences in concentrations measured during the various studies are expected because soil $CO_2$ is known to vary over time in response to dynamic environmental conditions such as temperature, rainfall, plant growth and microbial respiration (e.g. Luo and Zhou, 2006).

Methane concentrations were below atmospheric values (1.9 ppm) and ranged from non-detectable to 1.2 ppm compared to a maximum of 27 and 30 ppm reported by Petro-Find from their summer and winter studies, respectively. Methane values measured during the IPAC-CO2 study are more analogous to those recorded by the Weyburn-Midale $CO_2$ Monitoring and Storage Program, which report consistent values ranging from 0.5 to 2 ppm (Jones and Beaubien, 2005).

Additional fixed soil gases such as $O_2$, $N_2$, and Ar (not measured by Petro-Find) were investigated. During the study, $O_2$ ranged from near-atmospheric values of 20.5 to 11.6%. A general reverse association between $O_2$ and $CO_2$ was observed. Samples with higher $CO_2$ generally contained lower $O_2$. This type of trend in soils is widely known to result from biologic respiration (e.g. Hanson et al., 2000).

Figure 20:
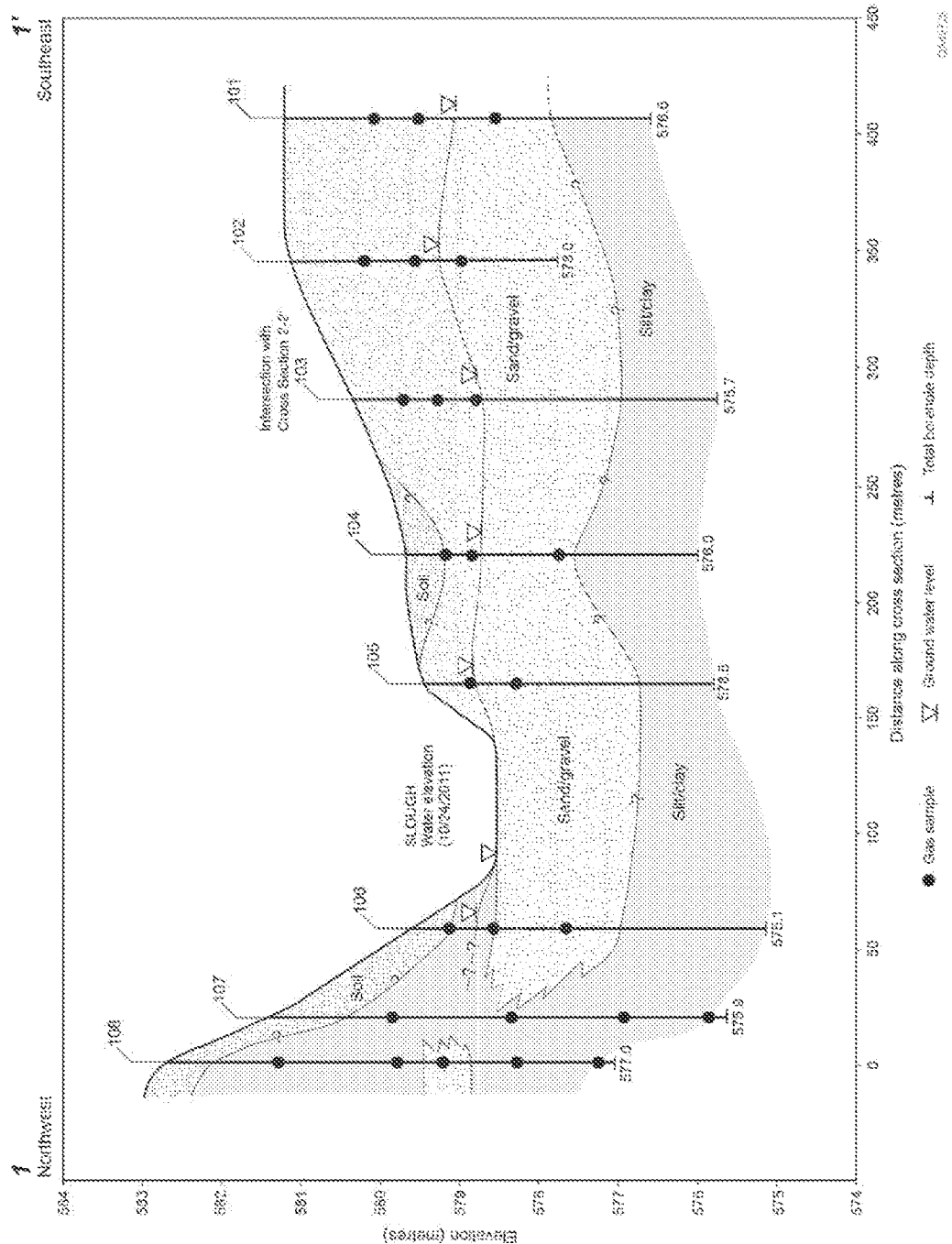
FIG. 20 is a hydrogeologic Cross Section 1-1' includes land surface and slough water elevation from Altus Geomatics (2011), generalized sedimentary lithology described from sediment samples collected during gas well borehole drilling, and inferred groundwater elevation estimated from the depth of saturated sediments in gas well boreholes (indicated by "wet" in Table 1). Sediments encountered during borehole drilling at station 107 were unsaturated; however, water was pumped from the gas well at a depth of 578.3 m. Sediments encountered during borehole drilling at stations 103 and 104 were saturated at 578.8 and 579.0 m (respectively); however, gas was collected from both stations 103 and 104 at 578.8 m.
Figure 21:
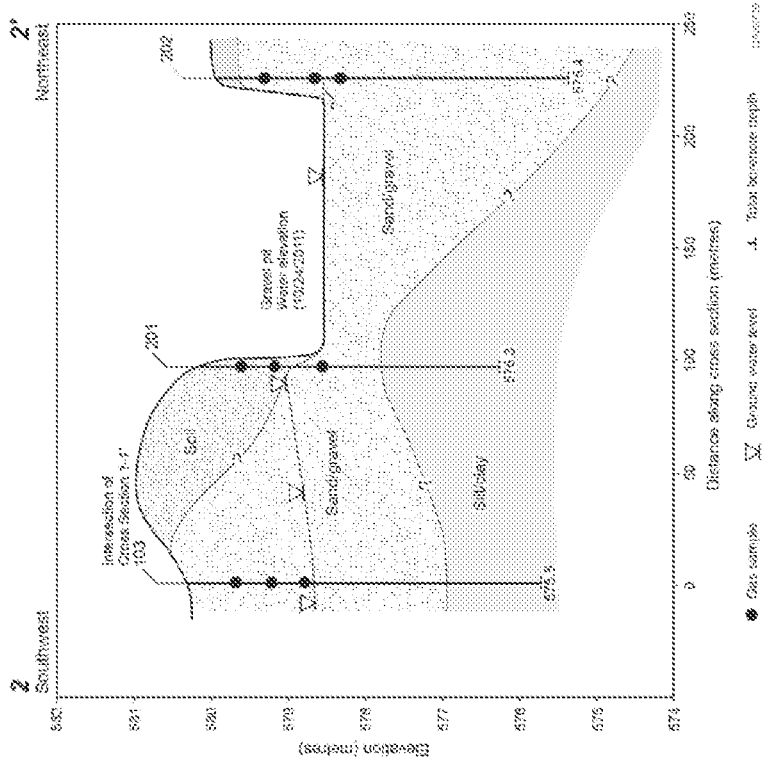
FIG. 21 is a hydrogeologic Cross Section 2-2' includes land surface and gravel pit water elevation from Altus Geomatics (2011), generalized sedimentary lithology described from sediment samples collected during gas well borehole drilling, and inferred groundwater elevation estimated from the depth of saturated sediments in gas well boreholes. Sediments encountered during borehole drilling at station 103 were saturated at 578.8 m; however, gas was collected from station 103 at 578.8 m. Sediments encountered during borehole drilling at station 202 were saturated below 0.91 m; however, gas was collected from all three gas wells constructed in the borehole.
Figure 22A:
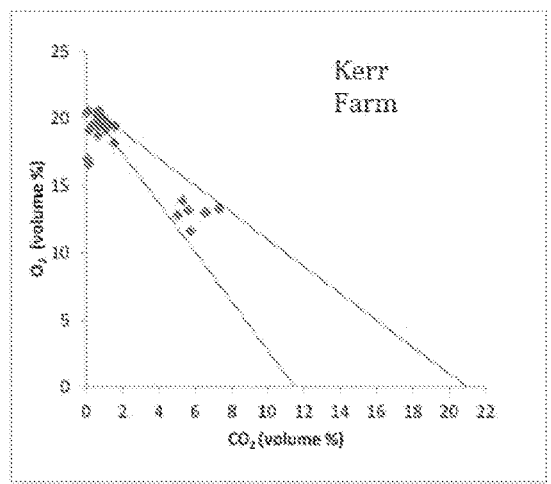
FIGS. 22A to 22D shows the $O_2$ versus $CO_2$ at the Kerr Farm and leakage proxy sites (ZERT and Mt. Etna) along with a graph showing the general fields for various background and leakage processes. The data indicate that soil gas on the Kerr property results from biologic respiration modified by dissolution of soil carbonate into recharging groundwater. Leakage proxies confirm that addition of exogenous $CO_2$ from outside the near-surface system would plot to the right of the biological respiration line, which is not the case at the Kerr site.
Figure 22B:
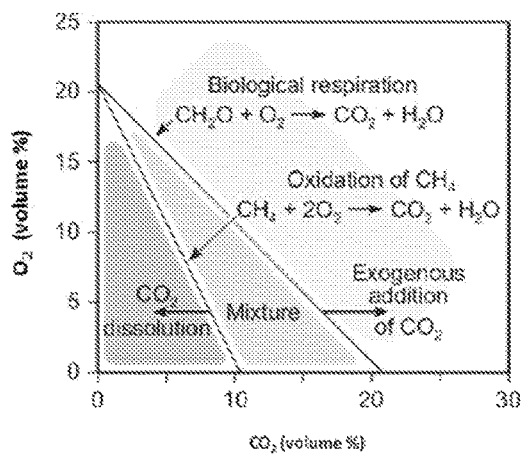
Figure 22C:
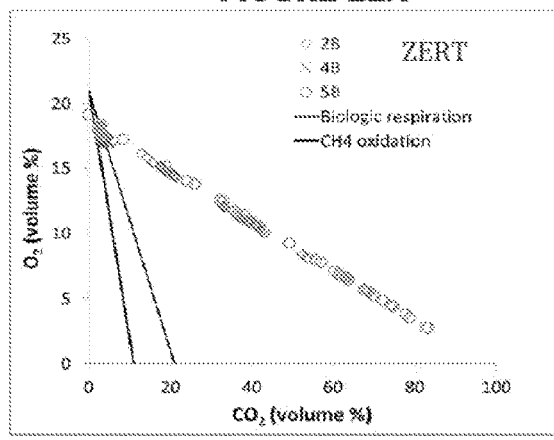
Figure 22D:
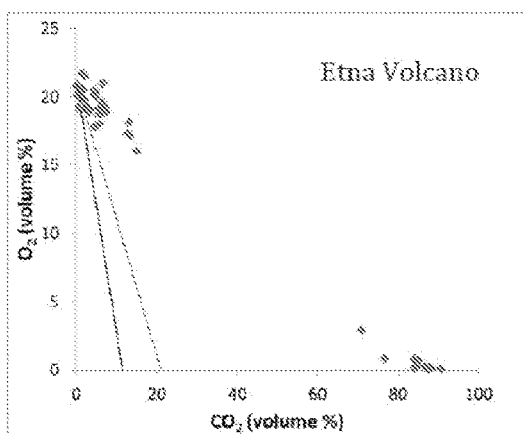
Figure 23A:
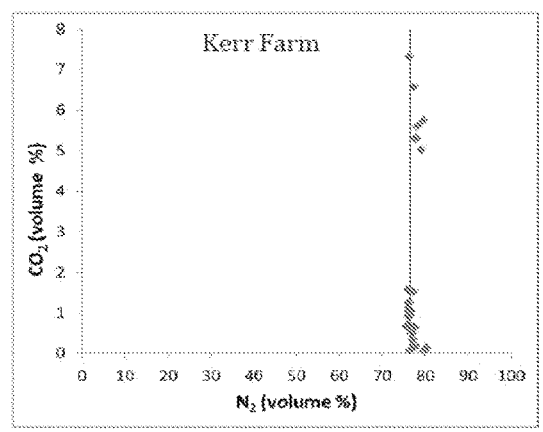
FIGS. 23A to 23D show the $CO_2$ versus $N_2$ at the Kerr Farm and leakage proxy sites (ZERT and Mt. Etna) along with a graph showing the general fields for various background and leakage processes. At the Kerr site, most samples cluster around atmospheric $N_2$ compositions with variable $CO_2$ concentrations. Some samples show $N_2$ compositions enriched relative to atmosphere, a gas signature that is attributed to subtraction of $CO_2$ through dissolution into recharging groundwater. These geochemical signatures are in contrast to those at the leakage proxy sites, which confirm that a leakage signal creates $N_2$ concentrations depleted relative to vapor-saturated atmosphere.
Figure 23B:
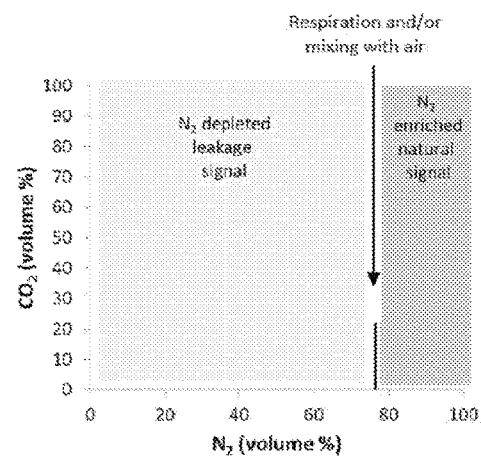
Figure 23C:
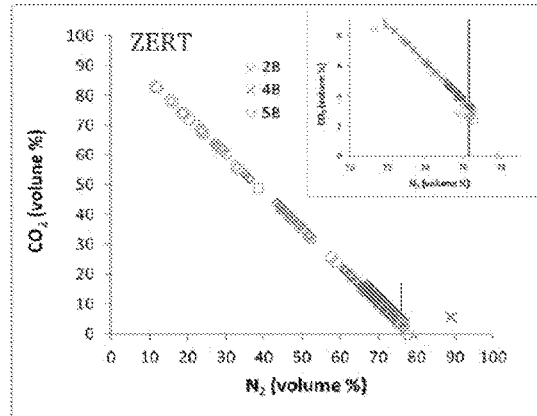
Figure 23D:
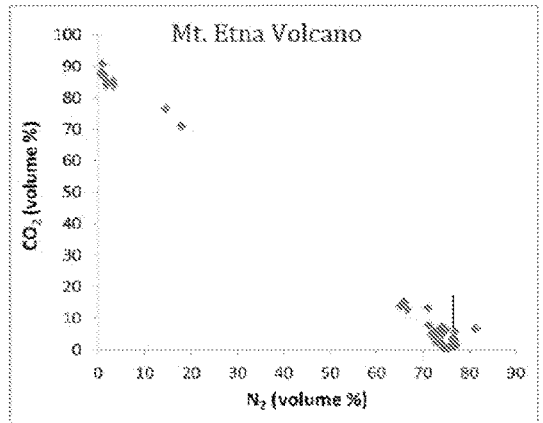
Figure 24A:
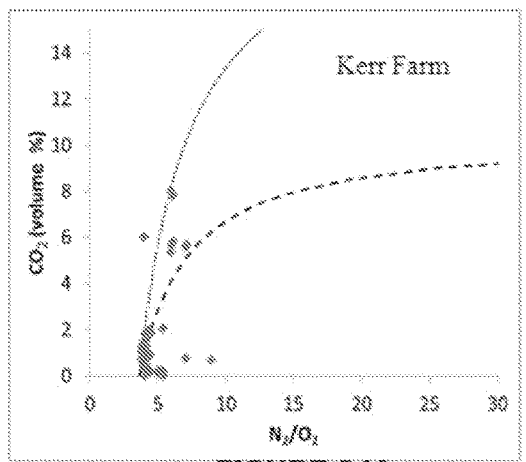
FIGS. 24A to 24D show the $CO_2$ versus $N_2/O_2$ at the Kerr Farm and leakage proxy sites (ZERT and Mt. Etna) along with a graph showing the general fields for various background and leakage processes. Note that the x axis for the Etna graph is in logarithmic scale to accommodate $N_2/O_2$ ratios that span 4 orders of magnitude. Kerr Farm samples are consistent with the processes of respiration and $CO_2$ dissolution as compared to the leakage proxies, which show $CO_2$ concentrations that are higher than would be produced by biologic trends.
Figure 24B:
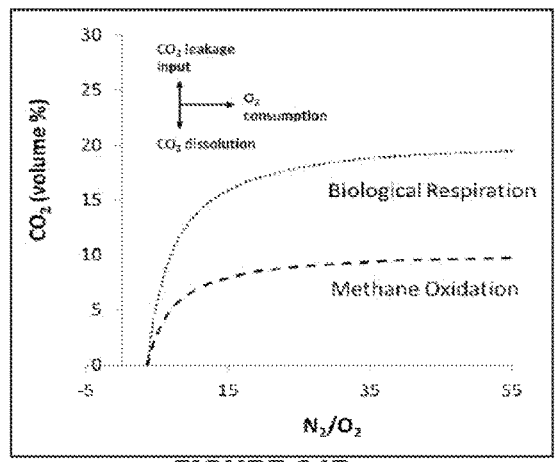
Figure 24C:
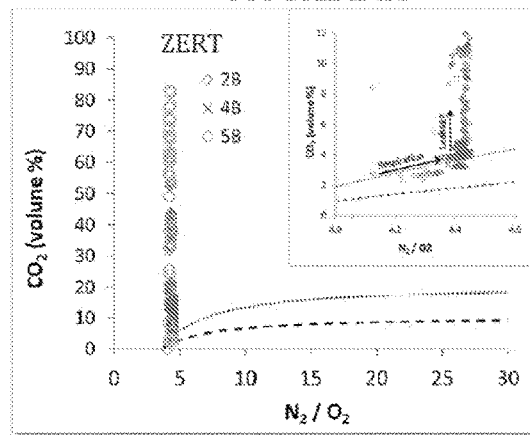
Figure 24D:
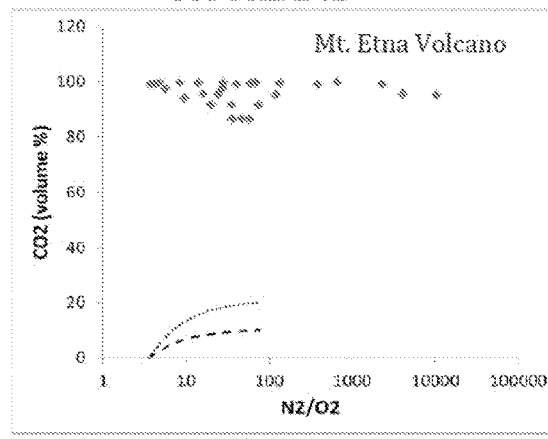

FIG. 20 is a hydrogeologic Cross Section 1-1' includes land surface and slough water elevation from Altus Geomatics (2011), generalized sedimentary lithology described from sediment samples collected during gas well borehole drilling, and inferred groundwater elevation estimated from the depth of saturated sediments in gas well boreholes (indicated by "wet" in Table 1). FIG. 21 is a hydrogeologic Cross Section 2-2' includes land surface and gravel pit water elevation from Altus Geomatics (2011), generalized sedimentary lithology described from sediment samples collected during gas well borehole drilling, and inferred groundwater elevation estimated from the depth of saturated sediments in gas well boreholes.

The $N_2$ at the Kerr site was generally enriched relative to soil atmospheric values and ranged from 75.7 to 81.4%. Normal atmosphere contains 78% $N_2$; however atmosphere in soil contains 76.4% $N_2$. This difference in $N_2$ concentrations is due to 2.2% water vapor that is normally retained even in dry soils at ambient conditions (Fredlund and Rahardjo, 1993). The existence of water vapor in the soil gas mixture dilutes, or decreases the percentage of N2 in that mixture relative to dry atmosphere. Extreme cases of denitrification may enrich $N_2$ above water-saturated atmospheric values (76.4%) but these cases are rare and can be identified by $Ar/N_2$ significantly less than 0.0119 (Martin et al, 1995). At the Kerr site, only one sample (station 202, 0.7 m) exhibits a $CO_2$ concentration that falls slightly beneath this value of 0.0119 indicating that widespread denitrification would not be responsible for any enriched $N_2$ values measured.

$O_2$ versus $CO_2$. A plot of $O_2$ versus $CO_2$ (FIGS. 22A-22D) shows that all gas samples from the Kerr study fall in geochemical fields indicating background processes, plotting along and below the line that represents bacterial respiration. If storage formation leakage were responsible for anomalous $CO_2$ gas concentrations at the Kerr farm, gas samples would be expected to lie to the right of the respiration line similar to what is observed at the ZERT site and Mt. Etna. Data collected at ZERT that fall along the biological respiration trend background signal fields were collected before $CO_2$ was released and data that fall in the leakage field were collected after $CO_2$ release. From these comparisons the $CO_2$ at the Kerr farm is not anomalous, but exhibits a natural background signature with $CO_2$ slightly below the biologic respiration trend. The same leakage signature is seen at Mt. Etna, where all samples impacted by volcanic $CO_2$ emanating from depth lie to the right of biological respiration line in the area of exogenous $CO_2$ addition. Here, compositions ranging from less-impacted soil gas (samples near 21% $O_2$ that plot near the biological respiration line), to nearly fully impacted (samples near 0% $O_2$ that plot to the far right of the biological respiration line).

$CO_2$ versus $N_2$. As previously discussed, $N_2$ is an inert gas and its concentration is most commonly affected only by addition or subtraction of a coexisting gas phase that will dilute or enrich the percentage of $N_2$, respectively, in the soil gas mixture. In the case of a leak from the storage formation entering the near-surface, $N_2$ values would become diluted relative to soil atmosphere; however, samples collected at the Kerr site are close or slightly enriched relative to the atmosphere (FIGS. 23A-23D). $N_2$ enrichment indicates subtraction of a gas component, namely by dissolution of $CO_2$ into recharging groundwater, which is a natural process. $CO_2$ dissolution is supported by the observation that samples with high $N_2$ also exhibit $CO_2$ concentrations that lie to the left of the respiration line in FIG. 8 due to $CO_2$ loss. In contrast, the N2 signature from ZERT controlled release site and the volcanic proxy show the opposite effect. Upon addition of exogenous $CO_2$, $N_2$ becomes strongly depleted relative to atmosphere in the soil gas mixture. This depletion increases in magnitude as the concentration of $CO_2$ in the soil gas approaches 100%. The differing results at the Kerr site compared to those at the leakage proxy sites confirm that $CO_2$ on the Kerr property does not originate from deep $CO_2$ leakage into the near-surface, but results from natural in-situ processes. Leakage proxies confirm that addition of exogenous CO2 from outside the near-surface system would plot to the right of the biological respiration line which is not the case at the Kerr site.

$CO_2$ versus $N_2/O_2$. Samples that lie below the respiration line in FIGS. 24A-24D may indicate either methane oxidation or dissolution of $CO_2$ into recharging groundwater, or both. A plot of $CO_2$ versus $N_2/O_2$ (FIGS. 24A-24D) can indirectly determine the degree to which methane oxidation contributes to $CO_2$ production by indicating $O_2$ consumption. $O_2$ is consumed both by biologic respiration and to a larger degree by $CH_4$ oxidation according to Eq. 1 and 2. CH4 oxidation can continue as long as $O_2$ is supplied to the system from influx of atmosphere into the soils. In some instances, $CH_4$ oxidation and $O_2$ influx can be rather vigorous resulting in $N_2/O_2$ orders of magnitude higher than the atmospheric value of 3.7. For example, $N_2/O_2$ values >250 were found at the West Texas playa lake where natural $CH_4$ concentrations were as high as 2% and biologic $CO_2$ was as high as 17%. N2/O2 values >750 were found at the Gulf Coast oilfield where $CH_4$ concentrations were as high as 33%, $CO_2$ was as high as 45%, and isotopic data indicated methane oxidation as the origin of $CO_2$ (Romanak et al., 2012). At the Kerr property, $N_2/O_2$ ranges from 3.7 to 6.9. Such small $N_2/O_2$ values together with a lack of $CH_4$ above atmospheric concentrations found at the site suggest a geochemistry influenced by biologic respiration with little or no $CH_4$ oxidation. Data from the Kerr Farm are therefore consistent with biologic respiration and dissolution of $CO_2$ into groundwater.

At the ZERT site, which is devoid of hydrocarbons, $N_2/O_2$ is relatively constant at near-atmospheric values, even when $CO_2$ is added to the system. The general trend of near-constant $N_2/O_2$ is an indicator that oxygen is not being significantly consumed and thus methane oxidation is not an important contributor to $CO_2$ concentrations. Magnification of a portion of the graph at the point where the $CO_2$ release began (inset in ZERT graph) shows pre-injection gas concentrations that lie along the biologic respiration line. As injected $CO_2$ reaches the monitoring well, gas concentrations leave the biologic respiration line and enter the leakage field. This observation is important because it suggests that, using this relationship, the amount of $CO_2$ attributed to leakage may be easily separated and quantified apart from the amount of $CO_2$ produced by respiration. Ways to separate and quantify a $CO_2$ leakage signal over natural $CO_2$ are not as readily apparent with other methods of leakage assessment that depend on background measurements to define natural $CO_2$ but have no way to define the processes affecting the $CO_2$.

At Mt. Etna $N_2/O_2$ ratios span 4 orders of magnitude. The high $CO_2$ concentrations and $N_2/O_2$ ratios are high enough to completely dampen out respiration and methane oxidation trends, presumably due to a high flux (<0.033 cm/second) of magmatic gases and high temperatures (<730° C.) that likely affect microbial populations. Giammanco et al. (1998) also report $CH_4$ concentrations in Mt. Etna gas samples ranging from non-detectable to as high as 12.2%. Such variable concentrations of $CH_4$ would be expected to result in different degrees of methane oxidation. Areas with low methane concentrations would experience less $CH_4$ oxidation and $O_2$ consumption resulting in low $N_2/O_2$ and areas with high $CH_4$ concentrations would experience more $CH_4$ oxidation and $O_2$ consumption resulting in high $N_2/O_2$ and $O_2$.

Figure 25:
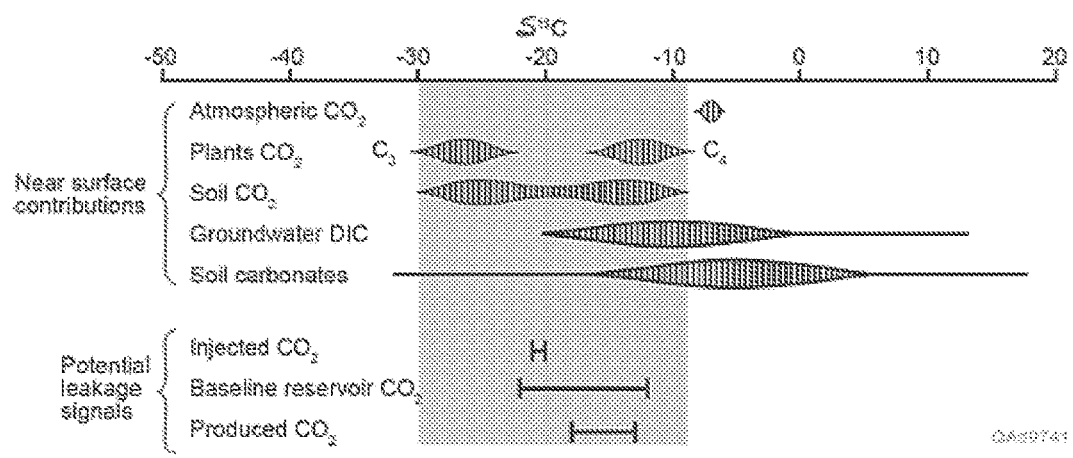
FIG. 25 shows the Carbon isotopic signatures of various potential natural $CO_2$ sources in the near-surface and of fluids from the Weyburn-Midale $CO_2$ storage reservoir. Shaded area indicates the range for natural soil $CO_2$ that fully overlaps all potential leakage signals. The overlap of signatures illustrates that injectate $CO_2$ cannot be distinguished from natural sources using $\delta^{13}C$ of $CO_2$ alone. (Figure is modified from Clark and Fritz, 1997, with data for potential leakage signals from Emberley et al., 2005).

Isotopes. Because reservoir-related isotopic ratios are not distinct from those of biologic respiration, isotopic signatures cannot be used to determine leakage at the Kerr Farm (FIG. 25) such as what was done in the Petro-Find study. $\delta 13C$ of $CO_2$ measured in the study ranges from −27.1 to −11.4‰. When compared to various sources of $CO_2$ gas within the near-surface this range best fits that of soil $CO_2$ (Clark and Fritz, 1997). However this isotopic range is not distinct from the various sources of $CO_2$ that could signal a leak from the reservoir including baseline reservoir gas before injection (−22 to −12‰), reservoir gas produced after injection (−18 to −13‰), and injectate $CO_2$ (−21 to −20‰) (Emberley et al., 2005).

Figure 26:
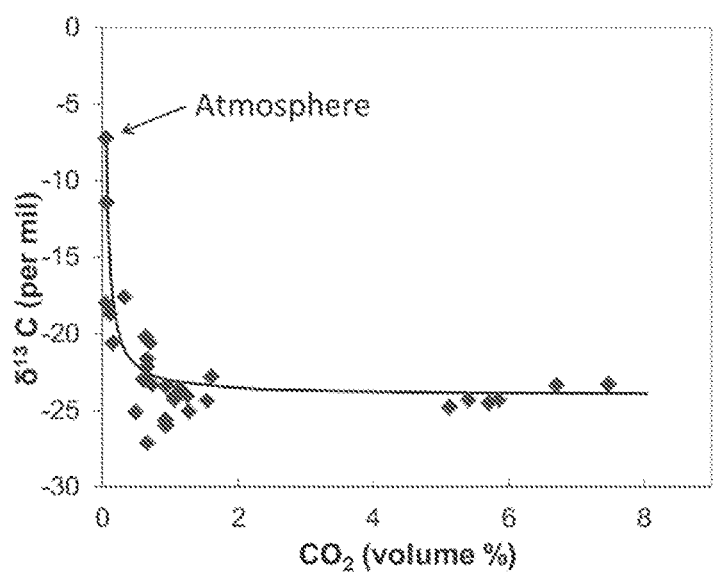
FIG. 26 is a graph that shows the $CO_2$ versus $\delta^{13}C$ of $CO_2$ illustrates that data fall along a mixing line between atmosphere and soil gas with a signature of −24‰. $\delta^{13}C$ ranging from −24 to −30‰ is consistent with biological respiration of $C_3$ plants and/or $CO_2$ respired from microbes utilizing $C_3$ plants as substrate.
Figure 27:
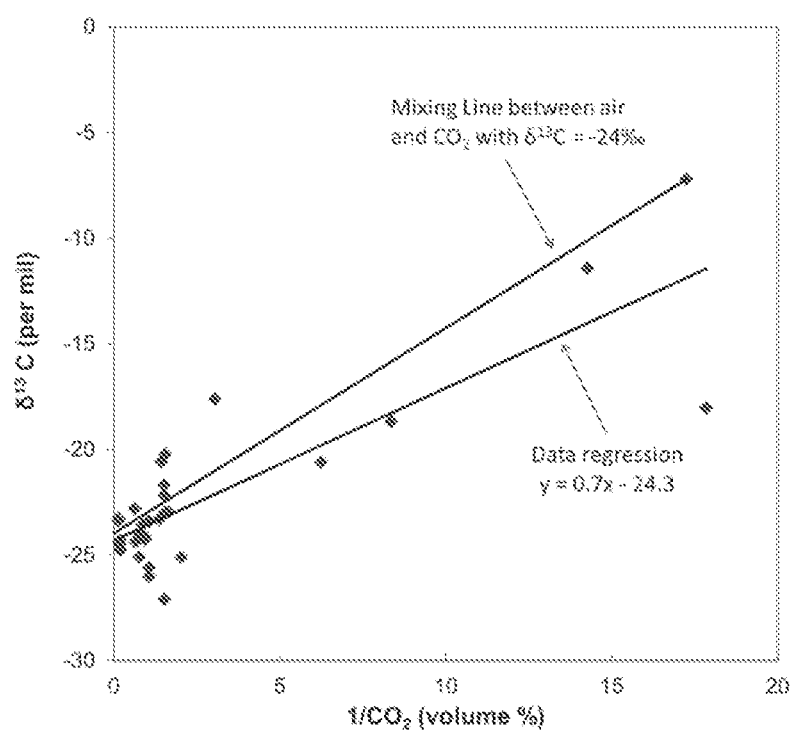
FIG. 27 is a Keeling plot that indicates the average carbon isotope composition of $CO_2$ respired at the Kerr Farm (represented by the y intercept of the linear data regression) of −24‰. A mixing line between air and a substrate of −24‰ yields results similar to the data regression indicating that isotopic variation of $CO_2$ is consistent with the processes of biologic respiration and atmospheric mixing. Dissolution of $CO_2$ and reaction with soil carbonate may fractionate the $\delta^{13}C$ of $CO_2$ by as much as 1.1‰ at 20° C. (Clark and Fritz (1997).

Variation of $\delta^{13}C$ with $CO_2$ concentration does yield useful information. $\delta 13C$ generally decreases with increases in $CO_2$ at the Kerr site (FIG. 26). This trend starts at atmosphere and bottoms out at an isotopic ratio of about −24‰, which is consistent with biologic respiration of C3 plants ($\delta 13C$=−24 to −30‰), which comprise the majority of plant species (Clark and Fritz, 1997). Biologic respiration can include plant root respiration or the respiration of microbes, which feed off organic matter formed by the degradation of C3 plants. A mixing curve between atmosphere and −24‰ nicely fits the data. In addition, linear data regression on a Keeling plot (FIG. 27) is traditionally used to determine the isotopic composition of ecosystem respiration (e.g. Pataki et al., 2003) and yields a $\delta^{13}C$ value of −24‰. The linear regression is similar and consistent with mixing between substrate of −24‰ and atmosphere, supporting the conclusion that CO2 on the Kerr property is the result of natural biologic respiration diluted to varying degrees with atmosphere, and not the result of leakage from the reservoir.

Hydrocarbons. FIG. 5 is a map showing gas sampling locations at the p-site, Cranfield oilfield. Data are reported for stations BG, 100, 101, 103. Additional drilling sites are labeled 102, 104, 105, 201, 202, 301, 302, 401 and 402. The main transect is indicated by the hashed line. Trace amounts of higher hydrocarbons (C2-C5) were detected both at stations considered to be background sites (stations 101 and 102) and at stations near the Petro-Find $CO_2$ anomalies (stations 104, 107, and 108) (Lafleur, 2010, 2011). Trace hydrocarbons also were found near the gravel pit at station 202, but not at gravel pit station 201. Higher hydrocarbons (C2-C5) also were measured by Petro-Find and the Weyburn-Midale Monitoring and Storage Project (Riding and Rochelle, 2005, 2009). Hydrocarbon gases most commonly originate from deep hydrocarbon seepage to the surface; however, they may result from bacterial respiration in the near-surface (Smith and Restall, 1971). Ethane, propane, ethylene, propylene, n- and iso-butane and butane-1 have been documented in natural soils under laboratory conditions and in waterlogged soils such as the prairie potholes of Saskatchewan (van Cleemput et al., 1983). The existence of hydrocarbons in soil at the Kerr property is therefore not necessarily inconsistent with evidence presented above that biologic respiration, not leakage from the storage reservoir, is the dominant process creating $CO_2$ at the site.

Fixed gas relationships and carbon isotope geochemistry of soil gas at the Kerr site strongly and consistently show that $CO_2$ on the Kerr property is biological in origin and not the result of leaks associated with the $CO_2$ storage reservoir. Traces of $C_2$-$C_5$ hydrocarbons, while not commonly a product of near-surface processes, have been documented to occur naturally in soils, and are therefore not problematic with the interpretation of a biological origin for gases. No evidence was found to suggest that gases originating in the deep subsurface have migrated to the near-surface. This conclusion is verified by comparing results to leakage proxy sites at Mt. Etna volcano and the ZERT controlled release facility which illustrate how a leakage signal would manifest using a process-based analysis. Evidence at the Kerr site clearly shows that $CO_2$ is from natural biologic respiration modified by mixing with atmosphere and dissolution of $CO_2$ into recharging groundwater. This evidence includes: 1) relationships between $CO_2$ and $O_2$ that indicate biologic respiration and dissolution of $CO_2$ into groundwater; 2) $N_2$ enriched above atmospheric concentrations; 3) low $N_2/O_2$ consistent with biologic respiration; and, 4) $\delta^{13}C$ of $CO_2$ that represents mixing of atmosphere with microbial and C3 plant respiration. The study confirms that a process-based approach can be used to quickly and economically assess leakage near geologic carbon storage sites. In addition, data from the ZERT release suggest quantification of a leakage signal apart from natural processes may be most easily accomplished using a process-based approach.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLES 1 AND 2

European Commission (2009), Directive 2009/31/EC of the European Parliament and of the Council of 23 Apr. 2009 on the geological storage of carbon dioxide: Official Journal of the European Union L 140/114 EN.

Fryar, A. E., S. A. Macko, W. F. Mullican, K. D. Romanak, and P. C. Bennett (2000), Nitrate reduction during ground-water recharge, Southern High Plains, Tex.: Journal of Contaminant Hydrology 40, 335-363.

Furche, M., S. Schlömer, E. Faber, and I. Dumke (2010), One year continuous vadose zone gas monitoring above an EGR test site Geophysical Research Abstracts Vol. 12, EGU2010-3095-1, 2010 7th EGU General Assembly 2010.

Gustayson, T. C., and D. A. Winkler (1988), Depositional facies of the Miocene-Pliocene Ogallala Formation, northwestern Texas and eastern New Mexico: Geology, 16(3): 203-206.

Hanson, P. J., N. T. Edwards, C. T. Garten, and J. A. Andrews (2000), Separating root and soil microbial contributions to soil respiration: A review of methods and observations: Biogeochemistry, 48: 115-146.

Hines, L., (1950), The Cranfield: World Oil, February: 131-146.

Hovorka, S. D., (1995), Quaternary evolution of playa lakes on the Southern High Plains—a case study from the Amarillo area, Texas: The University of Texas at Austin, Bureau of Economic Geology Report of Investigations No. 236, 52 p.

Konhauser, K. (2006), Introduction to geomicrobiology: Maldon, Oxford, Carlton: Blackwell Publishing, 425 p.

Luo, Y., and X. Zhou (2006), Soil respiration and the environment: Elsevier Academic Press Amsterdam, 334 p.

Mariotti, A., J. Germon, P. Hubert, P. Kaiser, R. Letolle, A. Tardieux, and P. Tardieux (1981), Experimental determination of nitrogen kinetic isotope fractionation: Some principles; illustration for the denitrification and nitrification processes: Plant and Soil 62(3): 413-430.

Martin, G. E., D. D. Snow, K. Euisik, and R. F. Spalding (1995), Simultaneous determination of Argon and Nitrogen: Ground Water 33(5): 781-785.

Nicot, J. P., and P. C. Bennett (1998), Gas phase dynamics of playa-wetlands: Journal of Environmental Engineering: 124: 1038-1046.

Osterkamp, W. R. and W. W. Wood (1987), Playa-lake basins on the Southern High Plains of Texas and New Mexico: Part 1: Hydrologic, geomorphic, and geologic evidence for their development: GSA Bulletin, 99: 215-223.

Riding, J. B., and C. A. Rochelle, (2009), Subsurface characterisation and geological monitoring of the CO2 injection operation at Weyburn, Saskatchewan, Canada in D. J. Evans and R. A. Chadwick, eds., Underground gas storage: worldwide experiences and future development in the UK and Europe: London, Geological Society, Special Publication 313: 227-256.

Romanak, K. D. (1997), Vadose-zone geochemistry of playa wetlands, High Plains, Tex.: The University of Texas at Austin, Ph.D. dissertation, 273 p.

Sherk, G. W., Romanak, K. D., Dale, J., Gilfillan, S. M. V., Haszeldine, R. S., Ringler, E. S., Wolaver, B. D., and Yang, C., (2011), The Kerr investigation: findings of the investigation into the impact of CO2 on the Kerr property: IPAC Research Inc., final report prepared for property owners Cameron and Jean Kerr, 181 p.

Scanlon, B. R., R. S. Goldsmith, and W. F. Mullican III (1997), Spatial variability in vadose flow beneath playa and adjacent interplaya settings and implications for contaminant transport, Southern High Plains, Tex.: The University of Texas at Austin, Bureau of Economic Geology Report of Investigations No. 243, 56 p.

Smith, K. A., and J. R. M. Arah, (1991), Gas chromatographic analysis of the soil atmosphere, in K. Smith, ed., Soil analysis: Marcel Dekker, New York, 505-546.

Strazisar, N. R., A. W. Wells, J. R. Diehl, R. W. Hammack, and G. A. Veloski, (2009), Near-surface monitoring for the ZERT shallow CO2 injection project: International Journal of Greenhouse Gas Control, 3(6): 736-744.

Striegl, R. G. and D. E. Armstrong, (1990), Carbon dioxide retention and carbon exchange on vadose Quaternary sediments: Geochimica et Cosmochimica Acta, 54(8): 2277-2283.

USEPA (2010a), General technical support document for injection and geologic sequestration of carbon dioxide: subparts RR and UU.

USEPA (2010b), Mandatory reporting of greenhouse gases: injection and geologic sequestration of carbon dioxide; final rule, 75 FR 75060.

Whalen, S. C., W. S. Reeburgh, and K. A. Sandbeck, (1990), Rapid methane oxidation in a landfill cover soil Applied Environmental Microbiology, 56(11): 3405-3411.

Whiticar, (1999), Carbon and hydrogen isotope systematics of bacterial formation and oxidation of methane: Chemical Geology, 161: 291-314.

REFERENCES-EXAMPLE 3

Altus Geomatics, 2011, IPAC CO2 Topographic Survey of S. W. ¼ Section of 30 Township 5—Range 13—W.2 Meridian. R. M. of Lomond No. 37. Survey Date: August 2011 to October 2011. Job Number 146036. Weyburn, S K: Altus Geomatics.

Aqua Terre Solutions Inc., 2006, Discussion of May 2, 2006 Water Quality Results at Domestic Water Well and Gravel Pit Water at Kerr Residence (SW 30-5-13 W2M). Calgary, A B: Aqua Terre Solutions Inc.

ASTM (American Society for Testing and Materials), 2011, ASTM D2487-11, Standard Practice for Classification of Soils for Engineering Purposes (Unified Soil Classification System). West Conshohocken, Pa.: ASTM International.

Beaubien, S., Strutt, M. H., Jones, D. G., Baubron, J.-C., Cardellini, C., Lombardi, S., Quattrochi, F. & I. Penner, 2004, D20 Report: Soil Gas surveys in the Weyburn oil field (2001-2003). Keyworth, Nottingham: British Geological Survey.

Beaubien, S. E., Jones, D. G., Gal, F., Barkwith, A. K. A. P., Braibant, G., Baubron, J.-C., Ciotoli, G., Graziani, S., Lister, T. R., Lombardi, S., Michel, K., Quattrocchi, F., & M. H. Strutt, 2013, Monitoring of near-surface gas geochemistry at the Weyburn, Canada, CO2-EOR site, 2001-2011; International Journal of Greenhouse Gas Control, Volume 16, Supplement 1, pp. S236-S262

Clark, I. D. & P. Fritz, 1997, Environmental Isotopes in Hydrogeology. Boca Raton, Fla.: CRC Press/Lewis Publishers.

EcoJustice, 2010, Site History, SW30-5-13-W2M Near Weyburn, Saskatchewan, Cameron and Jane Kerr. Calgary, A B: EcoJustice.

Emberley, S., Hutcheon, I. Shevalier, M., Durocher, K., Mayer, B., Gunter, W. D. & E. H. Perkins, 2005, Monitoring of fluid-rock interaction and $CO_2$ storage through produced fluid sampling at the Weyburn $CO_2$-injection enhanced oil recovery site, Saskatchewan, Canada. Applied Geochemistry, 20, 1131-1157.

Faber, E., Stahl, W. J. & M. J. Whiticar, 1992, Distinction of bacterial andthermogenic hydrocarbon gases, in R. Vially, ed., Bacterial Gas, Paris, Editions Technip, p. 63-74.

Fredlund, D. G. & H. Rahardjo. 1993. Soil Mechanics for Unsaturated Soils. New York, N.Y.: John Wiley & Sons, Inc.

Giammanco, S., Inguaggiato, S. & M. Valenza, 1998, Soil and fumaroles gases of Mount Etna Geochemistry and relations with volcanic activity. Journal of Volcanology and Geothermal Research, 81, 297-310.

Hackett, 0. M., Visher, F. N., McMurtrey, R. G., Steinhilber, W. L., Stermitz, Frank, Boner, F. C.& R. A. Krieger, 1960, Geology and ground-water resources of the Gallatin Valley, Gallatin County, Mont., with a section on Surface-water, and a section on chemical quality of the water USGS Water Supply Paper: 1482.

Hanson, P. J., Edwards, N. T., Garten, C. T. & J. A. Andrews, 2000, Separating root and soil microbial contributions to soil respiration: A review of methods and observations. Biogeochemistry, 48, 115-146.

Hardy Associates Ltd., 1985, Hydrogeology of the Weyburn Valley Aquifer, Saskatchewan. Submitted to: Saskatchewan Water Corporation under the Canada-Saskatchewan Interim Subsidiary Agreement on Water Development for Regional Economic Expansion and Drought Proofing.

Kharaka, Y. K., Thordsen, J. J., Kakouros, E., & G. Ambats, 2010, Changes in the chemistry of shallow groundwater related to the 2008 injection of CO2 at the ZERT field site, Bozeman, Mont., Environ Earth Sci (2010) 60:273-284.

Jones, D. G. & S. E. Beaubien, 2005, Continued Soil Gas Monitoring at the Weyburn Unit in 2004, Report No. COAL R288, DTI/Pub URN 05/1261. Keyworth, Nottingham, UK: British Geological Survey.

Jones, D. G., Strutt, M. H., Beaubien, S. E., Lombardi, S., Voltatorni, N., Baubron, J. C., Cardellini, C., Quattrocchi, F., Granieri, D.& L. Penner, 2003, Soil gas as a monitoring tool of deep geological storage of carbon dioxide: Results from the Encana EOR project in Weyburn, Saskatchewan (Canada). In The 226th American Chemical Society National Meeting, 7-11 Sep. 2003. New York, N.Y.: American Chemical Society.

Klusman, R. W., 2006, Detailed compositional analysis of gas seepage at the National Carbon Storage Test Site, Teapot Dome, Wyo., USA. Applied Geochemistry, v. 21, pp. 1498-1521.

Klusman, R. W., 2003a, Rate measurements and detection of gas microseepage to the atmosphere from an Enhanced Oil Recovery/sequestration project, Rangely, Colo., USA. Applied Geochemistry, v. 18, pp. 1825-1838.

Klusman, R. W., 2003b, Computer modeling of methanotrophic oxidation of hydrocarbons in the unsaturated zone from an Enhanced Oil Recovery/sequestration project, Rangely, Colo., USA. Applied Geochemistry, v. 18, pp. 1839-1852.

Klusman, R. W., 2011, Comparison of surface and near-surface geochemical methods for detection of gas microseepage from carbon dioxide sequestration, International Journal of Greenhouse Gas Control 5, 1369-1392.

Lafleur, P., 2010, Geochemical Soil Gas Survey: A Site Investigation of SW30-5-13-W2M Weyburn Field, Saskatchewan. Saskatoon, S K: Petro-Find Geochem Ltd.

Lafleur, P., 2011, Geochemical Soil Gas Survey: A Site Investigation of SW30-5-13-W2M, Weyburn Field, Saskatchewan, Monitoring Project Number 2. Saskatoon, S K: Petro-Find Geochem Ltd.

Luo, Y. & X. Zhou, 2006, Soil Respiration and the Environment. Amsterdam: Elsevier Academic Press.

Marrin, D. L., 1988, Soil gas sampling and misinterpretation, Ground Water Monitoring Rev., vol. 8, p. 51-54.

Marrin, D. L., 1991, Subsurface biogenic gas ratios associated with hydrocarbon contamination; in In-situ Bioreclamation, Stoneham, M A, Butterworth-Heinemann Publishers, p. 546-560.

Martin, G. E., Snow, D. D., E. Kim & R. F. Spalding, 1995, Simultaneous determination of Argon and Nitrogen. Ground Water, 33, 781-785.

Munsell Color Company, 1975, Munsell Soil Color Charts. Baltimore, Md.: Munsell Color Company.

Ostendorf, D. W., & Hampbell, D. H., 1991, Biodegradation of hydrocarbon vapors in the unsaturated zone: Water Resources Research, v.27, No. 4, p. 453-462.

Pataki, D. E., Ehleringer, J. R., Flanagan, L. B., Yakir, D., Bowling, D. R., Still, C., Buchmann, N., Kaplan, J. O. & J. A. Berry, 2003, The application and interpretation of Keeling plots in terrestrial carbon cycle research. Global Biogeochemical Cycles, 17, 22-1-22-14.

Petroleum Technology Research Centre, 2011, IEAGHG Weyburn-Midale $CO_2$ Monitoring and Storage Project—Response to a Soil Gas Study Performed by Petro-Find Geochem Ltd. Regina, S K: Petroleum Technology Research Centre, http://www.ptrc.ca/siteimages/WMP-Response-to-Petro-Find.pdf.

Poreda, R. J. & K. A. Farley, 1992, Rare gases in Samoan xenoliths. Earth and Planetary Science Letters, 113, 129-144.

Raistrick, M., Mayer, B., Shevalier, M., Perez, R. J., Hutcheon, I., Perkins, E. H. & W. D. Gunter, 2006, Using Chemical and Isotopic Data to Quantify Ionic Trapping of Injected Carbon Dioxide in Oil Field Brines. Environmental Science & Technology, 40, 6744-6749.

Rice, D. D., 1993, Biogenic gas: controls, habitats, and resource potential, in D. G. Howell, ed., The Future of Energy Gases—U.S. Geological Survey Professional Paper 1570, Washington, United States Government Printing Office, p. 583-606.

Riding, J. B. & C. A. Rochelle, 2005, The IEA Weyburn $CO_2$ Monitoring and Storage Project: Final report of the European research team. Keyworth, Nottingham, UK: British Geological Survey.

Riding, J. B. & C. A. Rochelle, 2009, Subsurface characterisation and geological monitoring of the $CO_2$ injection operation at Weyburn, Saskatchewan, Canada. In Underground Gas Storage: Worldwide Experiences and Future Development in the UK and Europe, Special Publication 313, eds. D. J. Evans & R. A. Chadwick, 227-256. London: Geological Society.

Ririe, G. T., and R. E. Sweeney, 1993, Comparison of hydrocarbon gases in soils from natural seeps and anthropogenic sources. Proc. 1993 Pet. Hydrocarbons Org. Chem. Ground Water: Prevent., Detect., Restor., Houston, Tex., 593 pp.

Romanak, K. D., 1997, Vadose-Zone Geochemistry of Playa Wetlands, High Plains, Tex., PhD Dissertation, 273 pp.

Romanak, K. D., Bennett, P. C., Yang, C. & S. D. Hovorka, 2012, Process-Based Approach to Soil Gas Monitoring at Geologic Carbon Storage Sites. Geophysical Research Letters. 60 (2), 227-239.

Romanak, K., Dobeck, L., Dixon, T., & L. Spangler, 2013, Potential for a Process-based Monitoring Method above Geologic Carbon Storage Sites using Dissolved Gases in Freshwater Aquifers. Procedia Earth and Planetary Science, 7, 746-749.

Saskatchewan Geological Survey, 2003, Geology and mineral and petroleum resources of Saskatchewan; Saskatchewan Industry and resources, Miscellaneous Report 2003-7, 173.

Saskatchewan Ministry of Energy and Resources, 2011, New Saskatchewan Stratigraphic Correlation Chart, internet resource, www.er.gov.sk.ca/stratchart.

Schoell, M., 1983, Genetic characterization of natural gases, AAPG Bulletin, v. 67, p. 2225-2238.

Schoell, M., 1988, Multiple origins of methane in the earth, Chemical Geology, v. 71, p. 1-10.

Simpson, M. A., 1993, Geology and Groundwater Resources of the Weyburn/Virden Area (62E/F), Saskatchewan. SRC Publication No. R-1210-3-E-93. Saskatoon, SK: Saskatchewan Research Council.

Smith, K. A. & S. W. F. Restall, 1971, The occurrence of ethylene in anaerobic soil. Journal of Soil Science, 22, 430-443.

Spangler L H, Dobeck, L. M., Repasky, K., Nehrir, A. et al., 2010, A controlled field pilot in Bozeman, Mont., USA, for testing near surface CO2 detection techniques and transport models. Environ Earth Sci 6.

Spangler, L. H., Dobeck, L. M., Repasky, K. S., Nehrir, A. R., Humphries, S. D., Barr, J. L., Keith, C. J., Shaw, J. A., Rouse, J. H., Cunningham, A. B., Benson, S. M., Oldenburg, C. M., Lewicki, J. L., Wells, A. W., Diehl, J. R., Strazisar, B. R., Fessenden, J. E., Rahn, T. A., Amonette, J. E., Barr, J. L., Pickles, W. L., Jacobson, J. D., Silver, E. A., Male, E. J., Rauch, H. W., Gullickson, K. S., Trautz, R., Kharaka, Y., Birkholzer, J., & L. Wielopolski., 2010. A shallow subsurface controlled release facility in Bozeman, Mont., USA, for testing near surface CO2 detection techniques and transport models. Environ. Earth Sci. 6.

Szatkowski, B., Whittaker, S., & B. Johnson, 2002, Identifying the source of migrating gases in surface casing vents and soils using stable carbon isotopes, Golden Lake Pool, West-central Saskatchewan, in Summary of Investigations 2002, vol. 1, Saskatchewan Geological Survey, Sask Industry and Resources, Misc. Report 2002-4.1, p. 118-125.

Tilley, B., and K. Muehlenbachs, 2006, Gas maturity and alteration systematics across the Western Canada Sedimentary Basin from four mud gas isotope depth profiles Organic Geochemistry, Volume 37, Issue 12, December 2006, Pages 1857-1868.

Trium Environmental Inc., 2011, Site assessment Weyburn Unit SW30-5-13W2; www.cenovus.com van Cleemput, 0., El-Sebaay, A. S. & L. Baert, 1983, Evolution of gaseous hydrocarbons from soil: Effect of moisture content and nitrate level. Soil Biology and Biochemistry, 15, 519-524.

Zhou, Z., Ballentine, C. J., Kipfer, R., Schoell, M. & S. Thibodeaux, 2005, Noble gas tracing of groundwater/coalbed methane interaction in the San Juan Basin, USA. Geochimica et Cosmochimica Acta, 69, 5413-5428.

Whiticar, M. J., 1994, Correlation of natural gases with their sources, in L. B. Magoon, and W. G. Dow, eds., The Petroleum System, From Source to Trap, AAPG, p. 261-283.

Whiticar, M. J., 1999, Carbon and hydrogen isotope systematics of bacterial formation and oxidation of methane, Chemical Geology 161, 291-314.

Whittaker, S., White, D., Law, D., & R. Chalaturnyk, 2004, IEAGHG Weyburn $CO_2$ Monitoring & Storage Project, Summary Report 2000-2004. In M. Wilson & M. Monea (Eds.), Proceedings of the 7th International Conference on Greenhouse Gas Control Technologies, Sep. 5-9, 2004, Vancouver, Canada (Vol. III). Regina, SK: Petroleum Technology Research Centre.

Whittaker, S., 2010, IEAGHG Weyburn-Midale $CO_2$ Storage & Monitoring Project, In Regional Carbon Sequestration Partnerships Annual Review, Oct. 5, 2010.

Wolayer, B. D., Hovorka, S. D., & R. C. Smyth, 2013, Greensites and brownsites: Implications for $CO_2$ sequestration characterization, risk assessment, and monitoring. International Journal of Greenhouse Gas Control, 19, 49-62.

Yang, C., Romanak, K., Hovorka, S., Trevino, R., 2013a. Modeling CO2 Release Experiment in the Shallow Subsurface and Sensitivity Analysis. Environmental & Engineering Geoscience, 19(3): 207-220.

Yang, C., Romanak, K., Hovorka, S., Holt, R. M., Lindner, J., Trevino, R., 2013b. Near-Surface Monitoring of Large-Volume CO2 Injection at Cranfield: Early Field Test of SECARB Phase III. SPE Journal, 18(3): 486-494.

What is claimed is:

1. A process-based method of detecting a $CO_2$ gas leak in a deep geologic gas storage reservoir, the method comprising:
    constructing a gas sampling station in a vadose zone proximal to the deep geologic gas storage reservoir;
    measuring a $CO_2$ level in the vadose zone using one or more gas analyzers sampling gas from the vadose zone through the gas sampling station;
    measuring an $O_2$ level in the vadose zone using one or more gas analyzers sampling gas from the vadose zone through the gas sampling station;
    measuring a $CH_4$ level in the vadose zone using one or more gas analyzers sampling gas from the vadose zone through the gas sampling station;
    measuring a $N_2$ level in the vadose zone using one or more gas analyzers sampling gas from the vadose zone through the gas sampling station;
    determining a $H_2O$ vapor level in the vadose zone;
    determining an Ar level in the vadose zone;
    computing a normalized $CO_2$ level, a normalized $O_2$ level, a normalized $CH_4$ level, a normalized $N_2$ level, a normalized Ar level, and a normalized $H_2O$ vapor level using the $CO_2$ level, the $O_2$ level, the $CH_4$ level, the $N_2$ level, the Ar level, and the $H_2O$ vapor level, wherein a normalized level corresponds to a concentration of a gas referenced to 100% by volume or to 1 atmosphere total pressure;
    determining a first relationship representing the normalized $O_2$ level as a function of the normalized $CO_2$ level;
    generating a comparison of the first relationship with a second relationship representing $O_2$ levels as a function of $CO_2$ levels for respiration processes;
    determining, using the comparison, that the first relationship is indicative of the normalized $CO_2$ level for the normalized $O_2$ level being greater than that expected for respiration, thereby detecting that $CO_2$ gas is being added to the vadose zone from an exogenous deep source;
    generating a second comparison of the first relationship with a third relationship representing $O_2$ levels as a function of $CO_2$ levels from $CH_4$ oxidation processes;
    determining, using the second comparison, that the first relationship is indicative of the normalized $CO_2$ level for the normalized $O_2$ level being greater than that expected from $CH_4$ oxidation, thereby confirming that $CO_2$ gas is being added to the vadose zone from the exogenous deep source; and indicating that $CO_2$ gas is leaking from the deep geologic gas storage reservoir.

2. The method of claim 1, wherein determining the first relationship includes generating a plot of the normalized $O_2$ level versus the normalized $CO_2$ level.

3. The method of claim 2, wherein generating the comparison includes showing a curve on the plot representing the second relationship.

4. The method of claim 1, wherein determining the first relationship includes generating a plot of the normalized $O_2$ level versus the normalized $CO_2$ level, and wherein generating the second comparison includes showing a curve on the plot representing the third relationship.

5. The method of claim 1, further comprising:
determining a third relationship representing the normalized $CO_2$ level as a function of the normalized $N_2$ level;
generating a second comparison of the third relationship with a normalized atmospheric $N_2$ level; and
determining, using the second comparison, that the normalized $N_2$ level is less than the normalized atmospheric $N_2$ level, thereby detecting that $CO_2$ gas is being added to the vadose zone from an exogenous deep source.

6. The method of claim 5, wherein determining the third relationship includes generating a second plot of the normalized $CO_2$ level versus the normalized $N_2$ level.

7. The method of claim 6, wherein generating the second comparison includes showing a line on the second plot representing the normalized atmospheric $N_2$ level.

8. The method of claim 1, further comprising:
determining a normalized $N_2/O_2$ level using the normalized $N_2$ level and the normalized $O_2$ level;
determining a third relationship of the normalized $CO_2$ level as a function of the normalized $N_2/O_2$ level;
generating a second comparison of the third relationship with a fourth relationship representing $CO_2$ levels as a function of $N_2/O_2$ levels for respiration or methane oxidation; and
determining, using the second comparison, that the third relationship is indicative of the normalized $CO_2$ level for the normalized $N_2/O_2$ level being greater than that expected for respiration or $CH_4$ oxidation, thereby detecting that $CO_2$ gas is being added to the vadose zone from an exogenous deep source.

9. The method of claim 8, wherein determining the third relationship includes generating a second plot of the normalized $CO_2$ level versus the normalized $N_2/O_2$ level.

10. The method of claim 9, wherein generating the second comparison includes showing a curve on the second plot representing the fourth relationship.

11. A process-based method of detecting a natural source of $CO_2$ gas proximal to a deep geologic gas storage reservoir, the method comprising:
constructing a gas sampling station in a vadose zone proximal to the deep geologic gas storage reservoir;
measuring a $CO_2$ level in the vadose zone using one or more gas analyzers sampling gas from the vadose zone through the gas sampling station;
measuring an $O_2$ level in the vadose zone using one or more gas analyzers sampling gas from the vadose zone through the gas sampling station;
measuring a $CH_4$ level in the vadose zone using one or more gas analyzers sampling gas from the vadose zone through the gas sampling station;
measuring a $N_2$ level in the vadose zone using one or more gas analyzers sampling gas from the vadose zone through the gas sampling station;
determining a $H_2O$ vapor level in the vadose zone;
determining an Ar level in the vadose zone;
computing a normalized $CO_2$ level, a normalized $O_2$ level, a normalized $CH_4$ level, a normalized $N_2$ level, a normalized Ar level, and a normalized $H_2O$ vapor level using the $CO_2$ level, the $O_2$ level, the $CH_4$ level, the $N_2$ level, the Ar level, and the $H_2O$ vapor level, wherein a normalized level corresponds to a concentration of a gas referenced to 100% by volume or to 1 atmosphere total pressure;
determining a first relationship representing the normalized $O_2$ level as a function of the normalized $CO_2$ level;
generating a comparison of the first relationship with a second relationship representing $O_2$ levels as a function of $CO_2$ levels for respiration processes;
determining, using the comparison, that the first relationship is indicative of the normalized $CO_2$ level for the normalized $O_2$ level being smaller or about equal to that expected for respiration, thereby detecting that $CO_2$ gas is being added to the vadose zone by a natural source;
generating a second comparison of the first relationship with a third relationship representing $O_2$ levels as a function of $CO_2$ levels from $CH_4$ oxidation processes;
determining, using the second comparison, that the first relationship is indicative of the normalized $CO_2$ level for the normalized $O_2$ level being smaller than or about equal to that expected from $CH_4$ oxidation, thereby confirming that $CO_2$ gas is being added to the vadose zone by the natural source; and
indicating that $CO_2$ gas present in the vadose zone is from a natural source.

12. The method of claim 11, further comprising:
identifying the natural source as biological respiration.

13. The method of claim 11, wherein determining the first relationship includes generating a plot of the normalized $O_2$ level versus the normalized $CO_2$ level.

14. The method of claim 13, wherein generating the comparison includes showing a curve on the plot representing the second relationship.

15. The method of claim 11, further comprising:
identifying the natural source as $CO_2$ from $CH_4$ oxidation.

16. The method of claim 11, wherein determining the first relationship includes generating a plot of the normalized $O_2$ level versus the normalized $CO_2$ level, and wherein generating the second comparison includes showing a curve on the plot representing the third relationship.

17. The method of claim 11, further comprising:
determining a third relationship representing the normalized $CO_2$ level as a function of the normalized $N_2$ level;
generating a second comparison of the third relationship with a normalized atmospheric $N_2$ level; and
determining, using the second comparison, that the normalized $N_2$ level is about equal to the normalized atmospheric $N_2$ level, thereby detecting that $CO_2$ gas is being added to the vadose zone from a natural source.

18. The method of claim 17, wherein determining the third relationship includes generating a second plot of the normalized $CO_2$ level versus the normalized $N_2$ level.

19. The method of claim 18, wherein generating the second comparison includes showing a line on the second plot representing the normalized atmospheric $N_2$ level.

20. The method of claim 11, further comprising:
determining a normalized $N_2/O_2$ level using the normalized $N_2$ level and the normalized $O_2$ level;

determining a third relationship of the normalized $CO_2$ level as a function of the normalized $N_2/O_2$ level;

generating a second comparison of the third relationship with a fourth relationship representing $CO_2$ levels as a function of $N_2/O_2$ levels for respiration or methane oxidation; and determining, using the second comparison, that the third relationship is indicative of the normalized $CO_2$ level for the normalized $N_2/O_2$ level being about equal to or less than that expected for respiration or $CH_4$ oxidation, thereby detecting that $CO_2$ gas is being added to the vadose zone from a natural source.

21. The method of claim 20, wherein determining the third relationship includes generating a second plot of the normalized $CO_2$ level versus the normalized $N_2/O_2$ level and wherein generating the second comparison includes showing a curve on the second plot representing the fourth relationship.

* * * * *